United States Patent
Ochiai et al.

(10) Patent No.: US 6,653,637 B2
(45) Date of Patent: Nov. 25, 2003

(54) X-RAY DETECTOR AND CHARGED-PARTICLE APPARATUS

(75) Inventors: Isao Ochiai, Otsuki (JP); Hiroyuki Shinada, Chofu (JP); Kimio Kanda, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 114 days.

(21) Appl. No.: 10/020,905

(22) Filed: Dec. 19, 2001

(65) Prior Publication Data

US 2002/0100877 A1 Aug. 1, 2002

(30) Foreign Application Priority Data

Jan. 26, 2001 (JP) ......................................... 2001-018427

(51) Int. Cl.[7] .............................. H01J 49/00; H01J 3/14; H01J 3/26; H01J 49/26; G01K 1/08; H05G 1/60
(52) U.S. Cl. ...................... 250/397; 250/281; 250/282; 250/299; 250/489; 378/19; 378/98.8
(58) Field of Search ........................... 378/19, 98.8, 43, 378/145; 250/281, 282, 292, 298, 299, 397, 489

(56) References Cited

U.S. PATENT DOCUMENTS 3,614,424 A * 10/1971 Openshaw .................. 250/310
5,044,001 A * 8/1991 Wang ........................... 378/43
5,326,970 A * 7/1994 Bayless .................... 250/269.1
5,903,004 A * 5/1999 Koshihara et al. .......... 250/310
6,160,263 A * 12/2000 Smith et al. .............. 250/493.1

FOREIGN PATENT DOCUMENTS

JP 08-222172 2/1995

OTHER PUBLICATIONS

Ray Ladbury, "Microcalorimeters May Provide a Solution to the Big Problem of Small Contaminants", Physics Today, Jul. 1998, pp. 19–21.
Peter J. Statham, "Measurement Performance of Energy–Dispersive X–Ray Systems", Microscopy and Microanalysis, 4, pp. 605–615, (1999).
The Structure of SEM and its Technology for High Resolution.

* cited by examiner

*Primary Examiner*—John R. Lee
*Assistant Examiner*—Mary El-Shammaa

(57) ABSTRACT

In a high-sensitivity X-ray detector, an image of the secondary electrons is little shifted and deformed by the astigmatism or the like even when it approaches very close to a specimen set on the stage of an electron microscope. When a beam of charged particles strike a specimen, the specimen emits backscattered charged particles along with X-rays. To prevent such undesired charged particles from entering into the X-ray detecting element of the X-ray detector, a means for generating a first magnetic field is applied. Another means for generating a second magnetic field is provided to cancel the magnetic filed leaked from the first means for generating magnetic field at the position of the specimen.

20 Claims, 17 Drawing Sheets

X-RAY DETECTOR AND CHARGED-PARTICLE APPARATUS

BACKGROUND OF THE INVENTION

1. Field of the Invention

The present invention relates to a charged particle trap for X-ray analysis so as to analyze a specimen and its constituent elements by sending a beam of charged particles to strike the specimen and detecting the characteristic X-rays from the specimen with least concern about any undesired charged particles.

2. Description of Related Art

A method for analyzing a specimen's elements by sending a beam of charged particles to strike the specimen and detecting the characteristic X-rays emitted from the specimen is known. An example of such method is the X-ray spectrometry of a spatial energy dispersive type in which the composition of a specimen is measured by detecting X-rays emitted from the specimen. This method is advantageous in that the characteristic X-rays from the specimen have energy equal to the electronic transitional energy of the elements constituting the specimen. The measurement of the volume of X-ray emissions per unit time for each X-ray provides information about how the specimen under examination is composed of elements. A semiconductor detector having semiconductor crystal such as silicon, germanium, etc. is generally used for detecting X-rays.

In recent years, as reported in Physics Today, July, 1998, pp. 10–21, an X-ray detector called a micro-calorimeter, which operates at ultra-low temperature (below 100 milli-Kelvin), has been developed. As compared with the above semiconductor detector, the micro-calorimeter detects the X-rays at high-energy resolution.

Along with the above-mentioned X-ray spectrometry of a spatial energy dispersive type, a method called X-ray spectrometry of a wavelength dispersive type using the combination of an X-ray spectrometer and a proportional counter is also known.

The schematic structural drawing of a typical radiation detector using the above-mentioned semiconductor detector is shown in FIG. 16. For noise reduction purposes, arrangement is made such that an X-ray crystal 101 and a field effect transistor 2 at the input stage of a pre-amplifier circuit block 20 is cooled to low temperature by a cryostat 7 using liquid nitrogen or a Peltier element in conjunction with cooling rods 12. When a beam of electrons 5 strikes a specimen 9, X-rays 1 are emitted from the specimen. The X-rays 1 pass through an X-ray window 8 and arrive at the X-ray crystal 101 where they are transformed into positive hole pairs of electrons proportional to the X-ray energy.

A method for processing signals produced by the X-ray crystal 101 will be described below. Electrons that reach at the electrodes of the X-ray crystal further travel through the pre-amplifier circuit block 20 of a charge integral type where they are transformed into pulses of voltage 220 with a height proportional to the number of the electrons. Furthermore, the pulses of voltage 220 are filtered through a shaping amplifier 51 so as to be shaped into pulses of voltage 310. The pulses of voltage 310 are inputted to a pulse height analyzer 53 where they are subjected to pulse height analysis and mapped in an X-ray spectrum 400. The X-ray spectrum 400 represents an energy distribution curve of the incident X-rays 1 detected by the X-ray crystal, i.e., how many X-rays of a certain energy level have been detected. The value of energy at a peak of the spectrum determines what is an element (a component) of the specimen and the count of the X-rays forming the spectrum peak determines the quantity of the element content.

Although, in the above description, attention is directed to the X-rays 1 emitted from the specimen 9 when the beam of electrons 5 strikes the specimen 9, reflected/back-scattered electrons 4 with a diversity of energy less than the energy of the incident electron beam also radiate from the specimen 9 by elastic or inelastic scattering. Such reflected electrons 4 are called backscattered electrons. When the backscattered electrons 4 are detected by the X-ray crystal as the incident rays, they are also transformed into electric signals as for the X-rays and cause background noise. Moreover, the backscattered electrons cause a defect in the X-ray crystal and significantly deteriorate the X-ray detecting performance of the X-ray crystal.

For the reason, a backscattered electron trap 3 is installed between the X-ray crystal 101 and the specimen 9, as shown in FIG. 16, so as to trap the backscattered electrons 4 from entering incidentally. Furthermore, as the backscattered electrons 4 strike against the surface of an object other than the specimen 9, X-rays are produced and cause more background noise.

Thus, a chamber 6 containing the X-ray crystal 101 is partially made of metal material to be thick enough to attenuate the X-rays so that the X-rays reflected from any objects other than the specimen will not enter into the X-ray crystal incidentally.

Another detector implementation mechanism is to keep the X-ray detector away from the specimen when the X-ray detection is not performed to further prevent the detector from being deteriorated by the backscattered electrons. Hereinafter, the backscattered electron trap will be referred to as an electron trap.

As described in Microscopy and Microanalysis, Vol. 4 (1999) pp. 605–615, for conventional X-ray detectors, a single X-ray crystal is generally used as the detector for detecting X-rays. The electron trap essentially consists of a pair of permanent magnets.

Another conventional electron trap is shown in FIGS. 17, 18, and 19. This trap has a structure similar to the trap disclosed in JP-A-103379/1981. FIG. 17 shows a section of the trap including the optical axis and the axis of X-ray detection. FIG. 18 shows another section of the trap taken along the line XVIII—XVIII in FIG. 17. FIG. 19 shows yet another section of the trap taken along the line XIX—XIX in FIG. 18.

The electron trap 300 includes two permanent magnets 21 and 22 placed above and under a X-ray path hole 11, a cylindrical support 15 made of soft iron with a magnetic path 13 and a groove 14, and a cover 16. A magnetic field 17 is generated in the X-ray path hole 11 so as to turn the incident backscattered electrons 4 to the hole 11 toward a direction perpendicular to the direction in which the electrons 4 travel and the direction of the magnetic field 17 by the Lorentz force. This causes the backscattered electrons to strike against the walls of the groove 14 so that they will not enter the X-ray crystal incidentally.

The groove 14 is formed such that X-rays 18 emitted when the backscattered electrons 4 strike against the walls of the groove 14 as shown in FIG. 19 will not enter the X-ray crystal 101 (see FIG. 16) incidentally. The magnetic flux density of the magnetic field is a few times larger than 0.1 tesla. If the magnetic flux density of the magnetic field is 0.2 tesla, electrons with energy of 20 keV incoming perpendicular to the magnet field is redirected to curve with the radius of curvature of about 2 millimeters.

The conventional X-ray detection by using a single X-ray detecting element has been illustrated above, FIGS. 20 and 21 illustrative an X-ray detector implementing a plurality of X-ray detecting units as disclosed in JP-A-222172/1996.

FIG. 20 shows the X-ray detector setup on an electron microscope, while four X-ray crystals 101 are set symmetrically on the right and left sides. These X-ray crystals 101 detect characteristic X-rays emitted from the specimen 9 when the beam of electrons 5 strikes the specimen. Reference numeral 107 denotes a collimator for reducing X-rays that travel in random directions.

FIG. 21 is an enlarged perspective view of the collimator shown in FIG. 20 for explaining two electron traps provided in the collimator for the innermost two X-ray crystals 101. The collimator 107 is made of tantalum and has an electron beam path hole 700 through which the electron beam 5 is allowed to travel along its axis. The hole is in the shape of a frustum of circular cone. There are a pair of X-ray path holes 74 and a pair of permanent magnets 270. The pair of permanent magnets 270 and a beryllium plate 72 are fit to the inner surfaces of each hole.

When the beam of electrons 5 strikes a specimen 9, characteristic X-rays 79 emitted from the specimen 9 enter into either of the X-ray crystals 101 incidentally and transformed into signals. Backscattered electrons 4 are also emitted from the specimen 9, which must be eliminated because they cause noise if they enter the X-ray crystals 101.

In the collimator structure shown in FIG. 21, on the side walls of each passage hole for leading characteristic X-rays to the X-ray crystals 101, a pair of permanent magnets 270, 270 are installed to face toward each other across the passage space. A magnetic field 17 generated by these permanent magnets 270, 270 turns the above backscattered electrons 4 inward so that the electrons will strike against the beryllium plate 72 so as to be absorbed thereon.

Meanwhile, to enhance the sensitivity of X-rays detection, it is effective to detect X-rays from the specimen under measurement from a large solid angle of detection. The solid angle of detection is determined by the distance from the specimen to the X-ray crystal and the X-ray sensitive area of the crystal. The shorter the distance, and the larger the sensitive area, the solid angle will be larger.

The image of a specimen observed by an electron microscope is provided by detecting secondary emissions of electrons and imaging processing.

FIG. 22 is a sectional view of an X-ray detector equipped with a conventional electron trap 300 for explaining the relation between the detector and a leakage magnetic field. Reference numerals 230 and 231 denote permanent magnets, reference numeral 11 denotes a X-ray path hole, 25 denotes a leakage magnetic field, 9 denotes a specimen, 10 denotes a point of electron irradiation, 8 denotes an X-ray window, 16 denotes a cover, and 101 denotes an X-ray crystal.

In the conventional electron trap, the leakage magnetic field exists in the axial direction of the electron trap 300 as shown in FIG. 22. Consequently, the shape of the cross section of the electron beam adjusted to a circular section is more deformed to a non-circular shape as the electron trap 300 as the traps get closer to the specimen due to the interaction between the electron beam and the leakage magnetic field. An aberration called an astigmatism occurs, which deforms the image obtained by secondary electron detection, and causes the imaging resolution to deteriorate.

The position of the point of electron irradiation 10 is determined by the interaction between the electron beam and the leakage magnetic field. Because the intensity of the leakage magnetic field 25 at this position changes as the electron trap gets closer to the specimen. Such a phenomenon shifts the point of electron irradiation 10, and consequently, the image of the secondary electrons shifts.

When the X-ray detector approaches the specimen 9, the image of the secondary electrons is more deformed and shifted as described above and thus correction is required. The correction becomes impossible at a certain distance between the detector and the specimen. Therefore, a limit is set to the distance to which the X-ray crystal 101 can approach the specimen 9, and it is difficult to set the solid angle of detection large.

Then, the diameter of the electron beam that is a main factor of determining the resolution of the image of the secondary electrons will be described below. FIG. 23 is a graph representing beam current versus beam diameter relation for an electron gun of a thermionic emission type (with a tungsten hairpin filament and a lanthanum hexaboride ($LAB_6$) point cathode) and an electron gun of a field emission (FE) type.

The graph shown in FIG. 23 is extracted from a reference "Electron Microscopy Technology" published by Tonomura Akira, Maruzen Co., Ltd., (1989) pp. 1–22. From this graph, it is apparent that the smaller the electron beam current, the smaller the beam diameter is. Normally, it is possible to observe an image of the secondary electrons if the beam current is at least $10^{-11}$ amperes. However, because of the limited distance between the X-ray detecting unit of the conventional X-ray detector and the specimen, the efficiency of X-ray detection is low. Thus, the beam of electrons to strike the analyte is generally about $2 \times 10^{-10}$ amperes, which is greater than the current applied when observing an image of the secondary electrons.

When a larger beam current is used, the beam diameter becomes larger as evident from FIG. 23 such that the imaging resolution decreases when an image of the secondary electrons is observed. Consequently, there is a trade off between the X-ray analysis and the resolution of the image of the secondary electrons, and these operations are usually carried out separately. As such, the operating conditions of the electron microscope must be adjusted to take measurements for each operation, which is troublesome and time-consuming.

On the other hand, the illustrated X-ray detector using a plurality of X-ray detecting units (FIGS. 20 and 21), the Prior Art, does have one advantage that the detection sensitivity can be multiplied as the number of the units increases. It may be possible for such a detector to perform X-ray analysis and observing a high-resolution image of the secondary electrons at the same time. However, the collimator structure of the electron traps of such a detector has a center hole for allowing the electron beam to pass and strike the analyte. The application of such a commonly used electron trap in X-ray detectors (essentially comprising a single X-ray detecting unit) is a question.

Another problem is that the collimator generates a large leakage magnetic field because the collimator essentially includes the holder made of nonmagnetic tantalum metal and permanent magnets.

SUMMARY OF THE INVENTION

The object of the present invention is to provide an X-ray detector having an electron trap performing such that an image of the secondary electrons is little deformed and shifted even if the detector gets to a specimen very close, and the electron trap is easily applicable to the conventional X-ray detectors essentially comprising a single X-ray detecting unit.

An X-ray detector and a charged-particle apparatus of the present invention achieve the above object based on the constitution of the invention described below.

The invention in one aspect is an X-ray detector comprising a specimen stage on which a specimen is rested, a charged particle beam irradiation unit for sending a beam of charged particles to strike the specimen set on the specimen stage, an X-ray crystal for detecting X-rays from the specimen by transforming the X-rays into electronic signals, a first pair of permanent magnets located across the path of the X-ray, another two pairs of permanent magnets, each pair of opposite magnets located on two ends of one of the first pair of permanent magnets while the two pairs of permanent magnets generate a magnetic field to cancel a leakage magnetic field generated by the first pair of permanent magnets at the point of irradiation.

The invention in another aspect is the discussed X-ray detector having the first pair of permanent magnets with their inner surfaces of opposite polarities facing toward each other and the other two pairs of permanent magnets are located such that their inner surface polarities facing toward each other are opposite and alternate with the polarities of the adjacent one of the first pair of permanent magnets.

The invention in a third aspect is the foregoing X-ray detector in which the magnetic force of the magnetic poles of the first pair of permanent magnets is substantially equal to the sum of the magnetic forces of the magnetic poles of the other two pairs of permanent magnets.

The invention in a fourth aspect is the foregoing X-ray detector in which the opposite surface area across the path hole of the first pair of permanent magnets is approximately double the parallel surface area of each of the other two pairs of permanent magnets.

The invention in a fifth aspect is the foregoing X-ray detector in which the first pair of permanent magnets and the other two pairs of permanent magnets are, separated by spacers made of a non-magnetic material.

The invention in a sixth aspect is the foregoing X-ray detector in which each of the first group of permanent magnets consists of four pieces of adjacent magnets of equal dimensions, and each of the other two groups of permanent magnets consists of two pieces of magnets of the same dimensions as the magnets of the first group.

The invention in a seventh aspect is a charged-particle apparatus characterized by comprising a specimen stage on which a specimen is rested, a source of charged particles, a scanning coil which scans the specimen set on said specimen stage with a beam of primary charged particles, an objective lens making the beam of charged particles strike the specimen, an electronic signal counter located between the objective lens and the specimen stage for counting the electronic signals outputted from the crystal, a display unit which displays an image of the electronic signals, while synchronizing signals from the electronic signal counter with the scanning signals that are input to the scanning coil, an X-ray detector including a pair of first permanent magnets across an X-ray path, two pairs of permanent magnets each pair of opposite polarities of which are located on one end of the first pair of external magnets along a direction parallel with the X-ray path. The two pairs of permanent magnets generate a magnetic field which cancels a leakage magnetic field generated by the first pair of permanent magnets at the specimen position, and a mechanism for moving/inching a charged particle beam irradiation relatively to the position of the charged particle trap.

The invention in an eighth aspect comprises an X-ray crystal, a first pair of permanent magnets placed above and below an X-ray path hole placed in front of said X-ray crystal such that their inner surfaces of opposite polarities facing toward each other across the path hole, a second pair of permanent magnets each placed on one end of one of said first pair of permanent magnets, and a third pair of permanent magnets each placed on one end of the other of said first pair of permanent magnets. The first pair of permanent magnets maybe divided into a plurality of pieces.

The invention in a ninth aspect comprises a specimen stage on which a specimen is rested, a source of charged particles, a scanning coil which scans the specimen set on the specimen stage with a beam of primary electrons from the source of electrons and an objective lens making the beam of primary electrons strike the specimen, a secondary electron detector located over the specimen stage to detect secondary electrons emitted from the specimen, a display unit for displaying an image of the electronic signals generated by the crystal, while synchronizing signals from the electronic signal counter with scanning signals that are input to the scanning coil, an X-ray crystal for transforming the X-rays emitted from the specimen into electronic signals, a first pair of permanent magnets located above and below an X-ray path hole, a second pair of permanent magnets each placed on one end of one of the first pair of permanent magnets, and a third pair of permanent magnets each placed on one end of the other of the first pair of permanent magnets, and a mechanism for moving/inching a charged particle beam irradiation area relatively to the position of the first pair of permanent magnets, i.e. the charged particle trap.

Other and further objects, features and advantages of the invention will appear more fully from the following description.

BRIEF DESCRIPTION OF THE DRAWINGS

The preferred embodiments of the present invention are illustrated in the accompanying drawings in which.

DETAILED DESCRIPTION OF THE PREFERRED EMBODIMENTS

With reference to the appended drawings, the preferred embodiments of the present invention are described.

(Embodiment 1)

First, the preferred Embodiment 1 of the present invention is described below.

Figure 1:
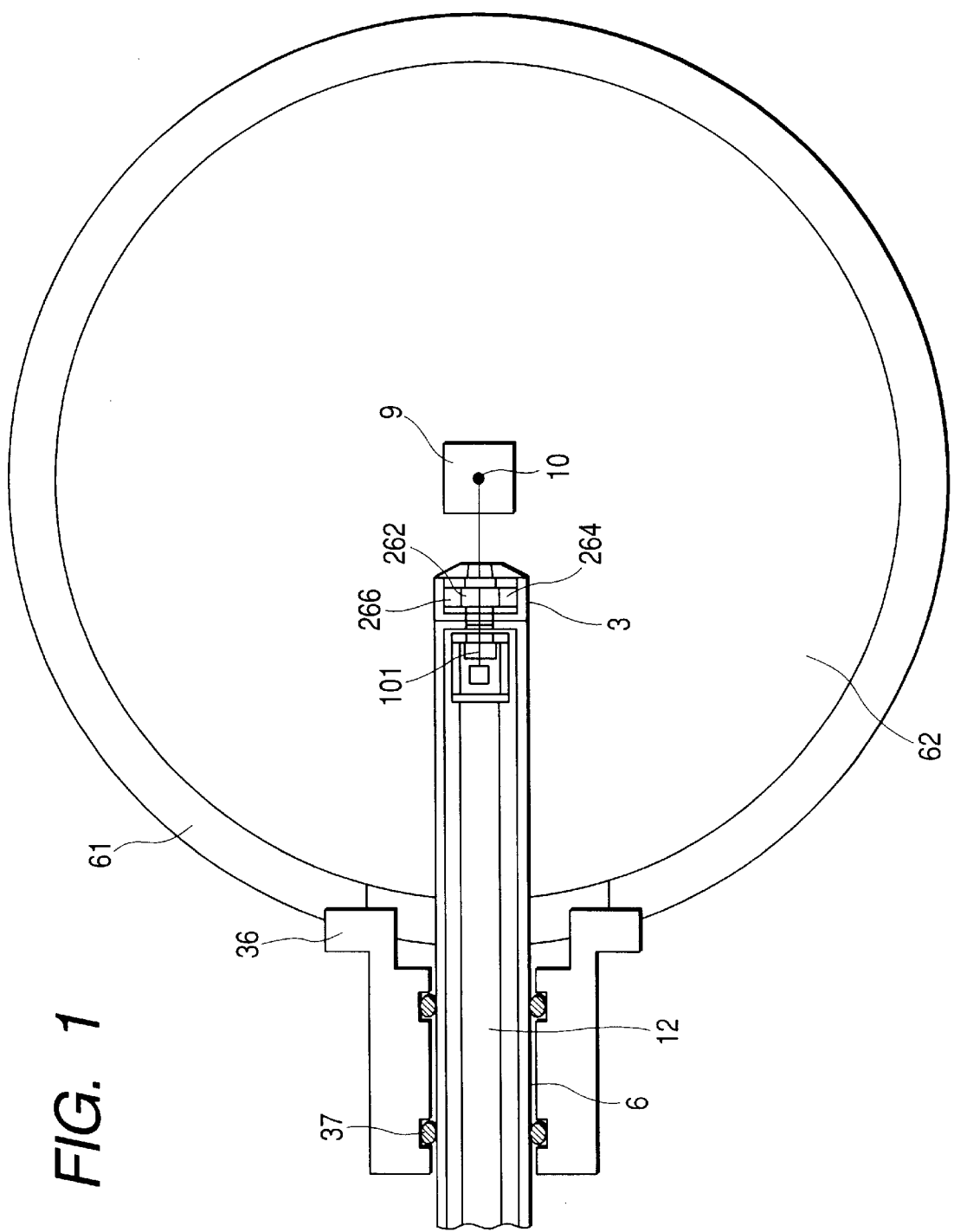
FIG. 1 is a sectional view showing the positional relation between an electron microscope and an X-ray detector embodied in accordance with the preferred Embodiment 1 of the present invention.
Figure 2:
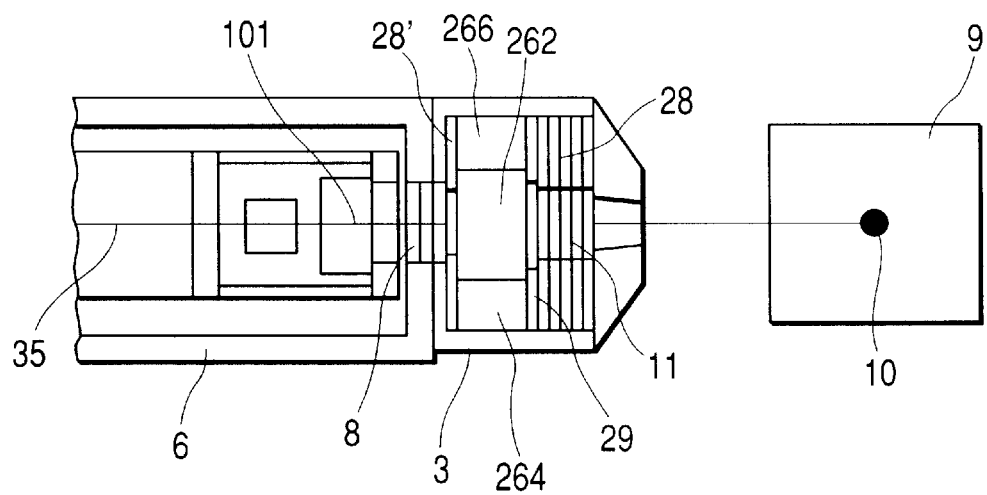
FIG. 2 is a sectional view showing the positional relation between a specimen set on the stage of the electron microscope and the tip of the X-ray detector of Embodiment 1 of the present invention.
Figure 3:
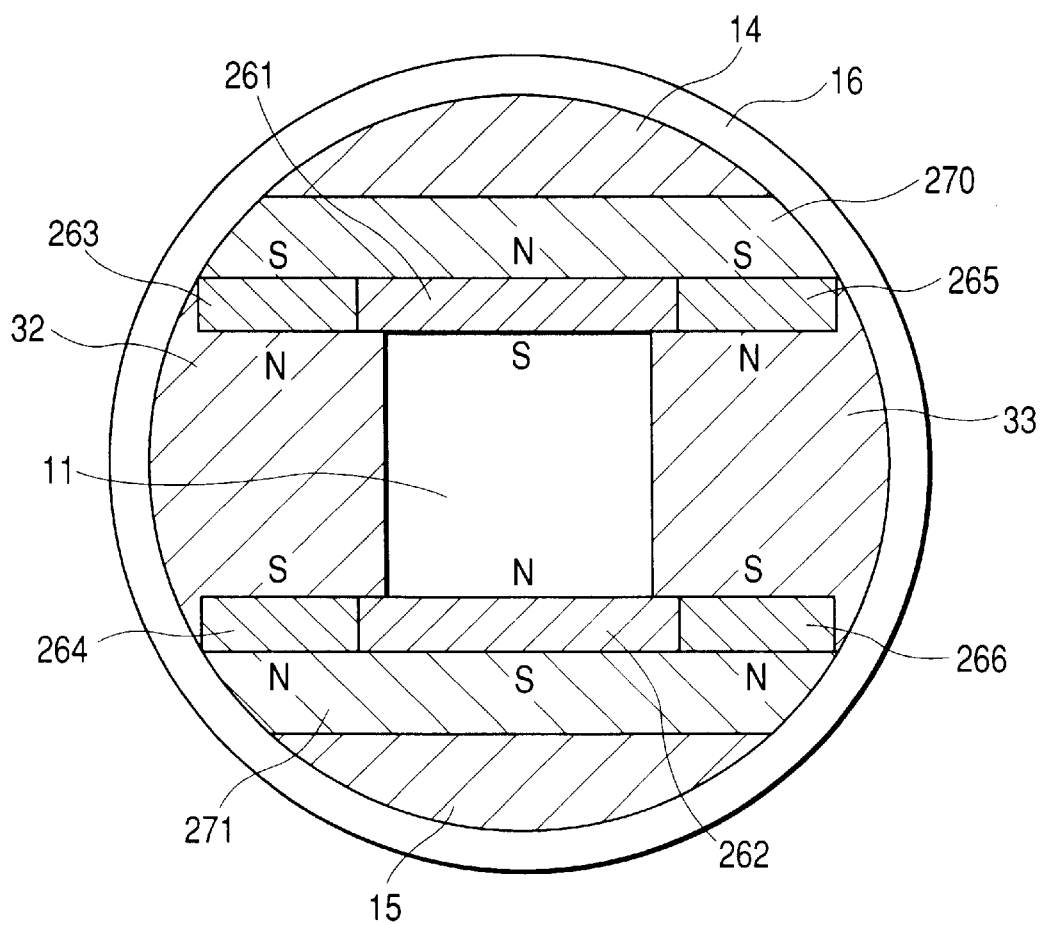
FIG. 3 is a cross sectional view of an electron trap embodied in accordance with Embodiment 1 of the present invention.
Figure 4:
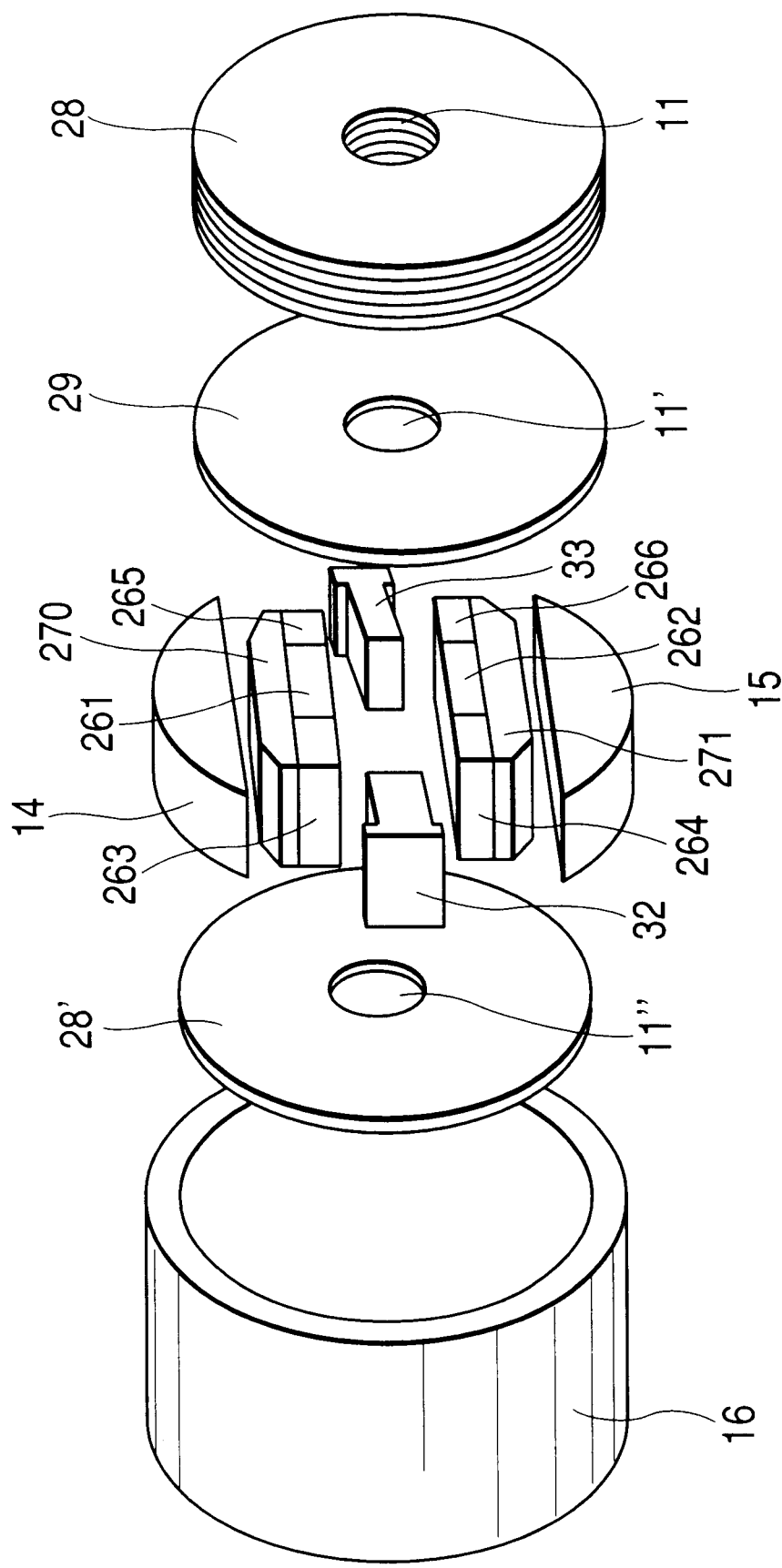
FIG. 4 is a perspective exploded view of the electron trap in FIG. 3.
Figure 5:
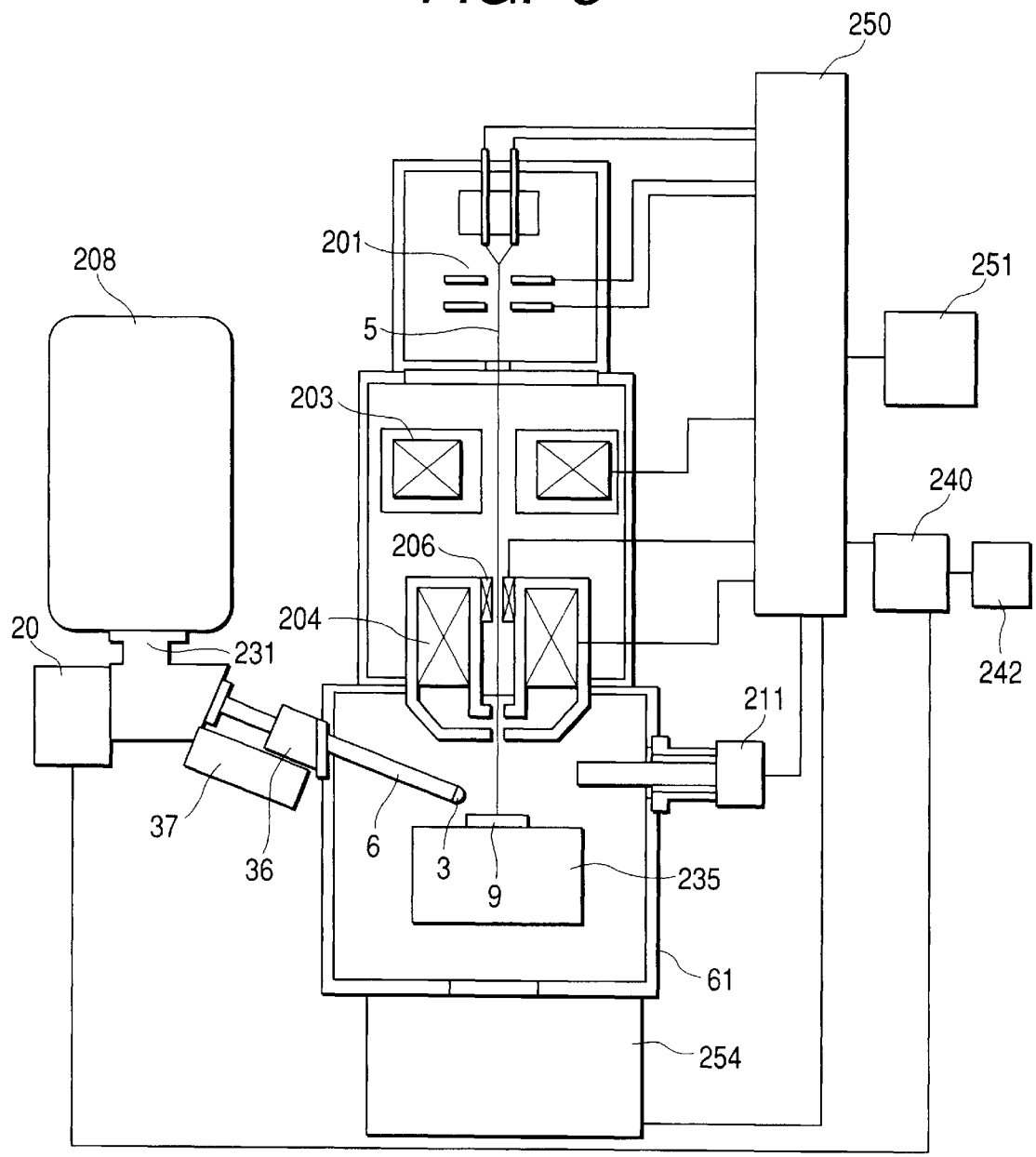
FIG. 5 is a schematic drawing showing the electron microscope on which the X-ray detector of Embodiment 1 of the present invention is mounted.
Figure 24:
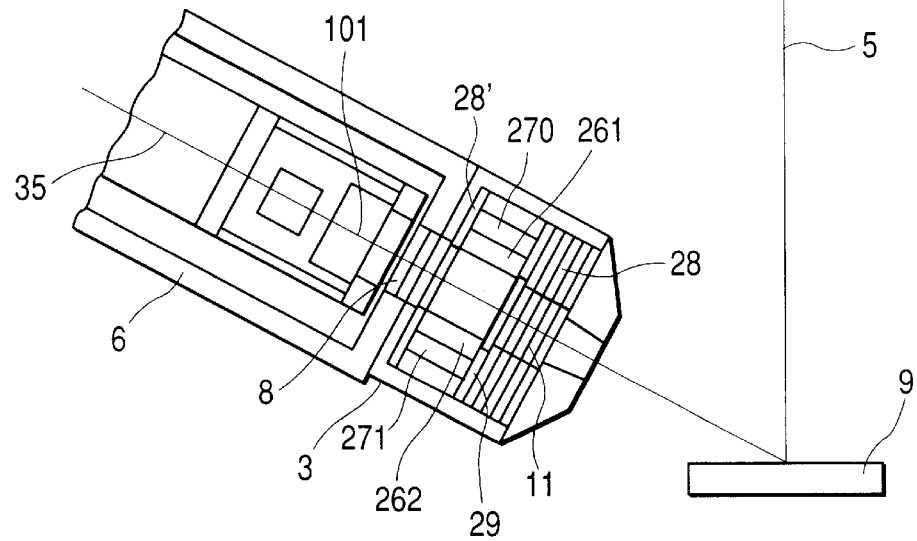
FIG. 24 is another sectional view of the electron trap of Embodiment 1 of the present invention.

FIG. 5 is a schematic diagram showing an electron microscope on which an X-ray detector mounted with an electron trap (preferred Embodiment 1 of the present invention). FIG. 1 shows the structure of a cross section of the tip of the X-ray detector including the electron trap embodied in accordance with the present invention and the positional relation between the tip and a specimen. FIG. 1 is an enlarged sectional view of the vertical plane taken along the axis a cylindrical chamber 6 shown in FIG. 5. FIG. 2 shows the structure of the tip of the X-ray detector and the positional relation between the tip and a specimen, which is a further enlarged sectional view of the tip shown in FIG. 1. FIG. 24 is a cross sectional view of the tip shown in FIG. 2. FIG. 3 is a vertical sectional view of the electron trap of the present invention, which shows the trap structure. FIG. 4 is a perspective exploded view of the electron trap of the present invention, which shows in detail how the trap is constructed.

The X-ray detector of Embodiment 1 has an electron trap 3 on its tip as shown in FIG. 1. The electron trap 3 uses the magnetic fields generated by two rectangular solid permanent magnets 261 and 262 positioned above and below the X-ray path hole 11, two permanent magnets 263 and 265 adjacent to a respective end of the magnet 261, and two permanent magnets 264 and 266 next to a respective end of the magnet 262 as shown in FIGS. 3 and 4.

The magnets 261 and 262 are of same dimensions. The thickness and longitudinal length (in the axial direction of the chamber 6) of the magnets 263–266 are the same as those of the magnet 261, and their transverse length is half that of the magnet 261. Thus, the magnetic force of the magnetic poles of the magnets 263–266 is half that of the magnet 261 or 262. In FIG. 3, X-rays are assumed to travel through the hole 11 in the direction penetrating into the plane of the cross section of the view. In FIG. 4, X-rays are assumed to travel in the direction from the right toward the left.

The magnets are positioned such that the orientations of their magnetic poles are as follows: the S pole surface of the magnet 261 and the N pole surface of the magnet 262 face toward each other, the N pole surface of the magnet 263 and the S pole surface of the magnet 264 face toward each other, and the N pole surface of the magnet 265 and the S pole surface of the magnet 266 face toward each other. The magnets 261, 263, and 265 are bonded to one magnetic path 270, and the magnets 262, 264, and 266 are bounded to another magnetic path 271.

In Embodiment 1, one end of the N pole of the magnet 261 is adjacent to the S pole of the magnet 263 and its other end is adjacent to the S pole of the magnet 265. One end of the S pole of the magnet 262 is adjacent to the N pole of the magnet 264 and its other end is adjacent to the N pole of the magnet 266. Thus, sufficient leakage prevention is provided in the magnetic paths 270 and 271 so that the magnetic field will not leak out.

The magnets 261 and 262 are positioned to face toward each other across a space, and the center of the space is aligned with the axis of the X-ray path hole 11. The magnetic field generated in the space between the magnet 261 and the magnet 262 turns the incident charged particles from the specimen toward the space aside by the Lorentz force so as to trap the particles. Thus, the charged particles cannot travel through the X-ray path hole 11.

As shown in FIG. 4, the magnets 261–266 bonded to the magnetic paths 270 and 271 are seated with spacers 32 and 33 and housed with spacers 14 and 15 in the cylindrical chamber 16. The material of the spacers 14, 15, 32, and 33 and the chamber 16 is non-magnetic aluminum.

The magnetic field intensity is weak at the boundary between the space between the magnet 261 and the magnet 262 and the space between the magnet 263 and the magnet 264 and at the boundary between the space between the magnet 261 and the magnet 262 and the space between the magnet 265 and the magnet 266. In view of the magnetic field distribution, at or near these boundaries, electron beam convergence takes place and most back-scattered or undesired electrons in the boundary zones pass without being turned aside. To avoid this, the spacers 32 and 33 are installed to slightly enter the space between the magnets 261 and 262 as shown in FIG. 3.

To further reduce the leakage of the magnetic field in the axial direction, a shield plate consisting of a lamination of five 0.5-mm thick permalloy discs with the center hole 11 is mounted to the front of the magnets 261–266 with a 0.5-mm thick aluminum disc 29 with the center hole 11' being fit between the shield plate and the magnets. The center holes 11 and 11' are circular and large enough to allow X-rays to pass through. Moreover, to the rear of the magnets, a 0.5-mm thick permalloy disk 28' with the center hole 11" is mounted.

Refer to FIG. 5 showing an electron microscope on which the X-ray detector equipped with the above-described electron trap 3 is mounted. In FIG. 5, reference numeral 201 denotes an electron gun, 5 denotes an electron beam, 203 denotes a condenser lens, 204 denotes an objective lens, 206 denotes a scanning coil, 211 denotes a secondary electron detector, 235 denotes a specimen stage, 250 denotes a controller of electron microscope, 251 denotes an I/O unit of electron microscope, and 254 denotes an evacuation system.

The X-ray detector comprises the above electron trap 3, a cylindrical chamber 6 in which an X-ray crystal is housed, a chamber 231, flanges 36, a moving mechanism 37, a liquid nitrogen reservoir 208, a circuit block of pre-amplifier 20, an X-ray pulse processor 240, and an I/O unit 242. The chamber 6 and the chamber 231 are evacuated and sealed. The moving mechanism 37 is worked to protrude or retract the tip of the X-ray detector with respect to the specimen. Using this mechanism, the operator can make the tip approach a specimen 9 when measurement is made and keep the tip away from the specimen when measurement is not performed.

Scanning the specimen with the electron beam is performed by the scanning coil 206 and secondary electrons emitted from the specimen 9 are detected by the secondary electron detector 211. The pulses from the detected electrons are processed and displayed on the I/O unit 251, so that the morphology of the specimen 9 will be observed. The X-ray detector detects radiated X-rays that go up sideways and the thus detected X-rays are subjected to X-ray energy analysis by which the elemental structure of the specimen 9 is analyzed. By scanning with the electron beam and performing the X-ray analysis, two-dimensional elemental distribution analysis of the specimen 9 is achieved.

FIG. 1 is an enlarged outline sectional view of the vertical plane cut along the axis the cylindrical chamber 6 shown in FIG. 5. On the tip of the cylindrical chamber 6, the electron trap 3 of the present invention is installed. The cooling rods 6, the X-ray crystal 101, and the flanges 36 are installed symmetrically with respect to the axis of the cylindrical chamber 6. FIG. 2 is an enlarged view of the tip of the X-ray detector and the specimen shown in FIG. 1.

In Embodiment 1 of the present invention, the size of the magnets 263–266 is half the size of the magnets 261 and 262, i.e., the magnetic force of the magnetic poles of the former magnets is half that of the latter magnets. The magnet 261 and magnet 262 generate a leakage magnetic field on the specimen stage. A half part of the leakage magnetic field is cancelled by the magnets 263 and 264 and its remaining half is cancelled by the magnets 265 and 266. As such, the leakage magnetic field is substantially eliminated to zero. This is a noticeable feature of the present invention.

When the magnets 261 and 262 that are 1-mm thick, 5.5-mm wide, and 5-mm long rectangular solid blocks of rare-earth ferromagnetic material and the magnets 263–266 that are 1-mm thick, 2.75-mm wide, and 5-mm long rectangular solid blocks of the same material, a magnetic flux density about 0.3 tesla is measured in the center of the X-ray path hole 11. Here, both the distance between the inner surfaces of the permanent magnets 261 and 262 and the distance between the inner surfaces of the spacers 32 and 33 are about 3.5 mm. When the X-ray detector with such an electron trap is applied to an electron microscope with the capability of an acceleration voltage of 25 kilovolts and measurement is made with the X-ray crystal with an effective area of 10 mm square, the influence of the backscattered electrons is less than the minimum scale of the measurement.

Figure 7:
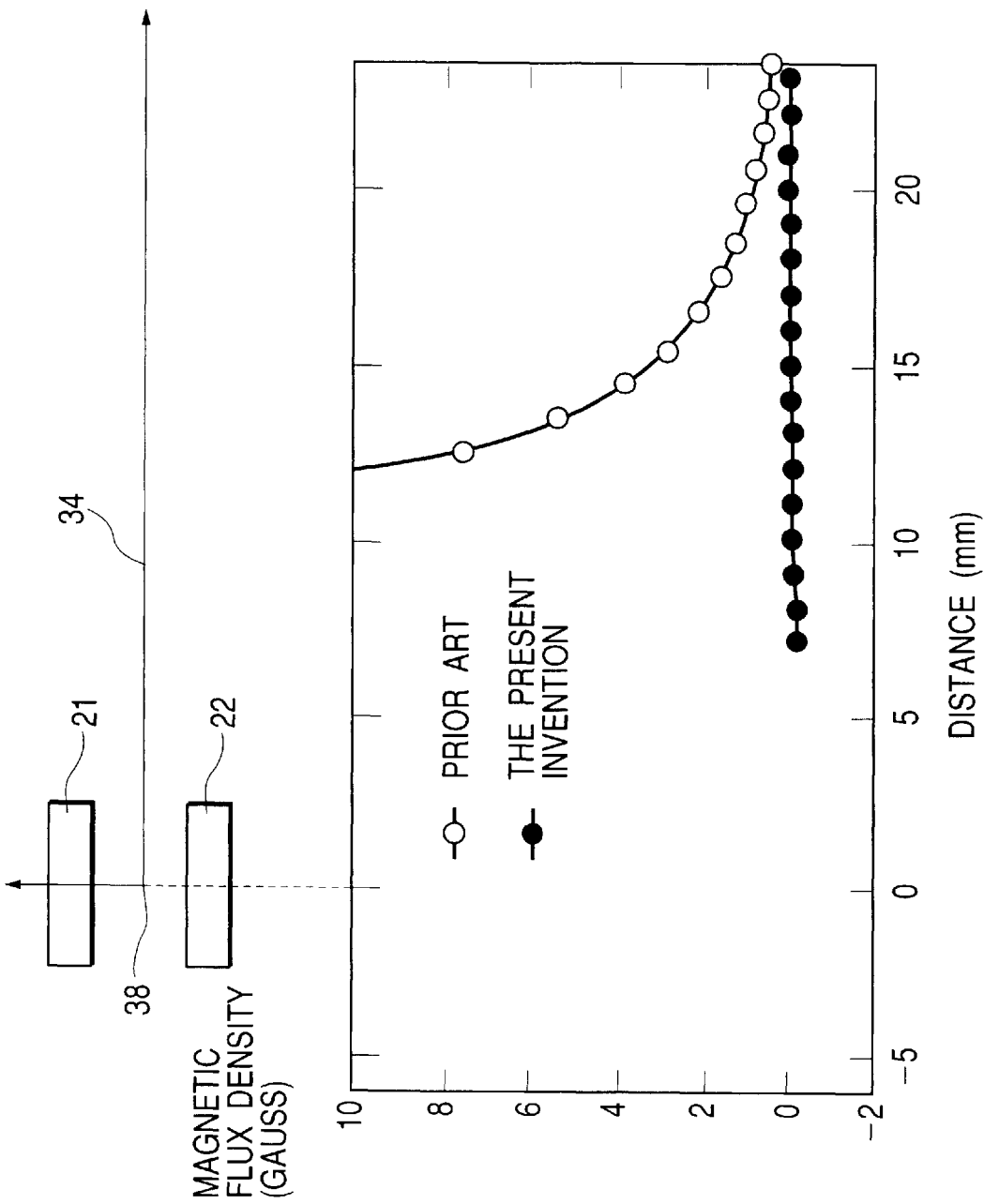
FIG. 7 is a graph demonstrating the relative leakage current distribution for the electron trap of the present invention and that of a conventional electron trap.
Figure 17:
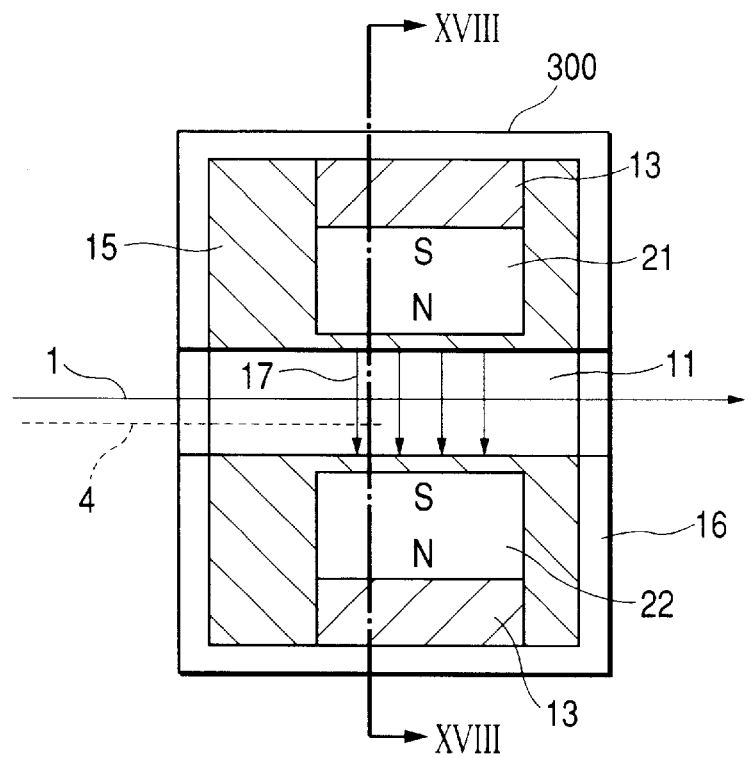
FIG. 17 is a vertical sectional view of a conventional type of electron trap.
Figure 18:
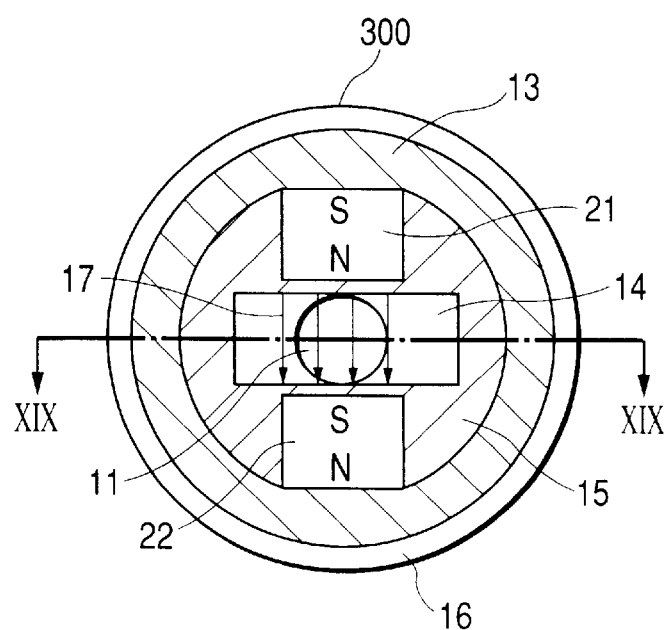
FIG. 18 is another cross sectional view of the conventional type of electron trap.
Figure 19:
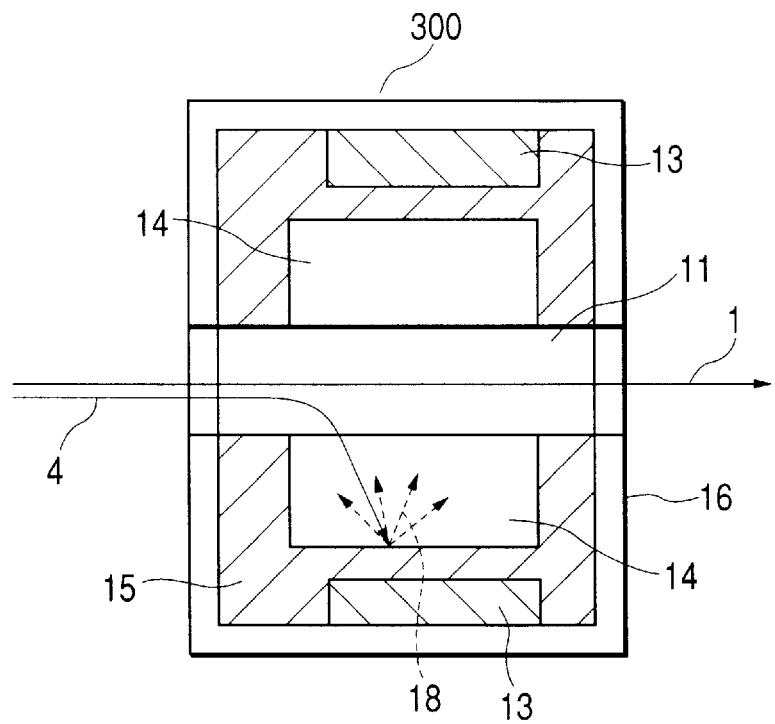
FIG. 19 is a horizontal sectional view of the conventional type of electron trap.
Figure 20:
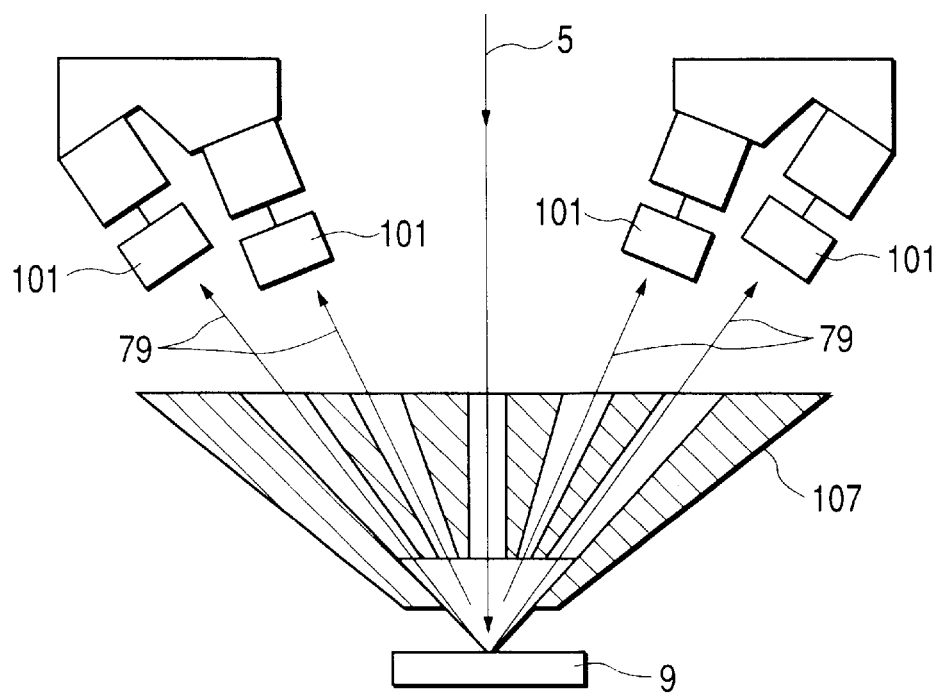
FIG. 20 is a sectional view of an electron microscope on which another conventional type of electron traps is mounted.
Figure 21:
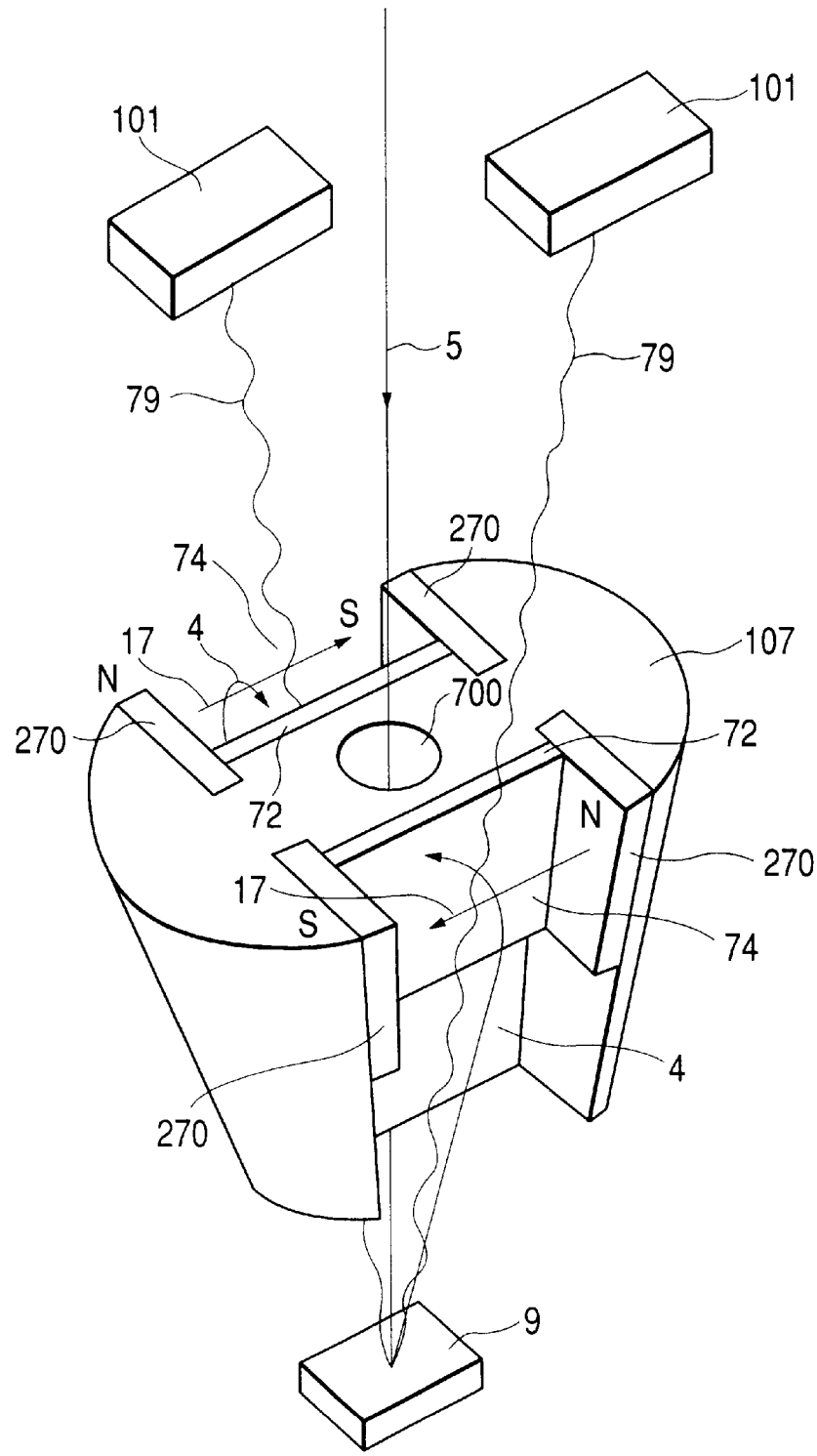
FIG. 21 is a view illustrative of another conventional type of electron trap.

Refer to a graph shown in FIG. 7, wherein a line with solid black dots corresponds to the distribution of the leakage magnetic field from the electron trap 3 in Embodiment 1. The scales on the X-axis indicate distance in the axial direction from the center of the electron trap and the scales on the y-axis indicate magnetic flux density measured with a gauss meter using a Hall-effect element. For comparison, FIG. 7 includes a line with white circles corresponding to the leakage magnetic field measured on the conventional electron trap as shown in FIGS. 17 and 18. The black dots and white circles indicate measurement data.

In the X-ray detector of Embodiment 1, two magnets are coupled onto each end of the magnets 261 and 262, i.e., a total of four magnets 263, 264, 265, and 266 whose magnetic pole polarity is opposite to the polarity of the magnetic pole of the magnets 261 and 262 such that magnetic forces of half of the magnets 261 and 262 are placed adjacent to either of the magnet 261 or 262. Under such an arrangement, the permanent magnets cancel their magnetic fields at the point of X-ray irradiation. Thus, around the point of electron irradiation on the specimen, i.e. at the point of irradiation and between the specimen and the tip of the objective lens, the leakage magnetic field generated by all permanent magnets is very small in comparison with the conventional electron trap and substantially zero near the inlet of the electron trap.

This effect significantly reduces the disadvantage described in the section of Prior Art, such as that an image of the secondary electrons is shifted, deformed, or out of focus by the astigmatism when the X-ray detector gets close to the specimen. By applying the electron trap of the present invention, the distance from the tip of the trap to the specimen, which is limited to about 25 mm or longer in the prior art, is reduced to 5 mm in the present invention. When the tip of the electron trap of the present invention approached so close to the specimen, the degree of correction made for the shift and astigmatism of the image of the secondary electrons is the same as that of correction made when the tip of the conventional electron trap approached the specimen to 25 mm away from the specimen.

According to the experiment carried out by the inventor, despite of the substantially zero leakage magnetic field, the shift and astigmatism of the image of the secondary electrons are not zero. It is believed that this is caused by a weak leakage magnetic field generated between the objective lens and the specimen stage and this magnetic field is changed by the magnetic bodies, namely, the permanent magnets and magnetic paths in the electron trap.

The deformation of a magnetic field by inserting a magnetic body into the magnetic field depends on the outside diameter rather than the volume of the magnetic body. If magnetic bodies with the same outside diameter enter the magnetic field, their influence on the magnetic field is the same whether they are solid or hollow. Contrary to the cylindrical magnetic path of the conventional electron trap described in the section of Prior Art, the electron trap of Embodiment 1 includes two semi-cylindrical magnetic paths, each being formed for each opposite set of three magnets in the above-described arrangement of six magnets.

When a magnetic body enters a magnetic field, the degree of the magnetic field change is generally determined by the outside dimension rather than the volume of the magnetic body. The greater the outside dimension, the greater the magnetic field changes. Because the outside dimension of the magnetic paths in Embodiment 1 is smaller than that of the magnetic paths in the prior-art, the electron trap of Embodiment 1 reduces the influence on the magnetic field from the objective lens.

While reducing the distance from the tip of the electron trap to the specimen, the X-ray crystal is installed with its surface exposed to X-rays perpendicular to the X-ray path line. Consequentially, the distance from the specimen to the crystal is reduced from about 40 mm, which is a typical value measured by the conventional X-ray detectors, to 16 mm. The solid angle of detection becomes six times larger than that of conventional X-ray detectors. In addition, the X-ray detector of Embodiment 1 multiplies the detection sensitivity by 2.5 times than that of the conventional X-ray detectors under the same measurement time condition or reduces the measurement time to one sixth or less than the conventional X-ray detectors under the same measurement condition.

Figure 23:
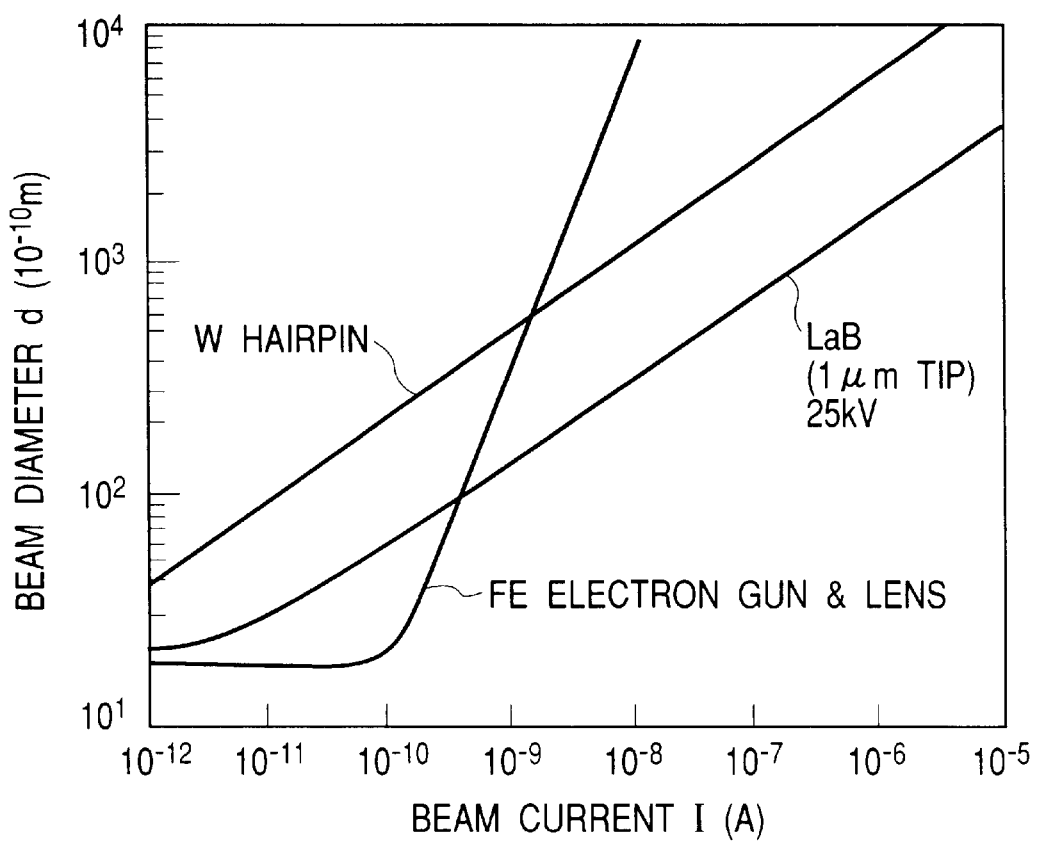
FIG. 23 is a graph representing the beam current versua beam diameter relation of a beam of electrons used in an electron microscope.

Under the same measurement time condition, the beam current required to gain the same detection sensitivity as the conventional X-ray detectors becomes one sixth or less. The X-ray detector of Embodiment 1 reduces the beam current of about $2 \times 10^{-10}$ amperes used by a conventional X-ray detector to $4 \times 10^{-11}$ or below amperes. Consequently, a high-resolution image of the secondary electrons is obtained while X-ray measurement is carried out, as apparent from the beam current versua beam diameter relation shown in FIG. 23.

Figure 22:
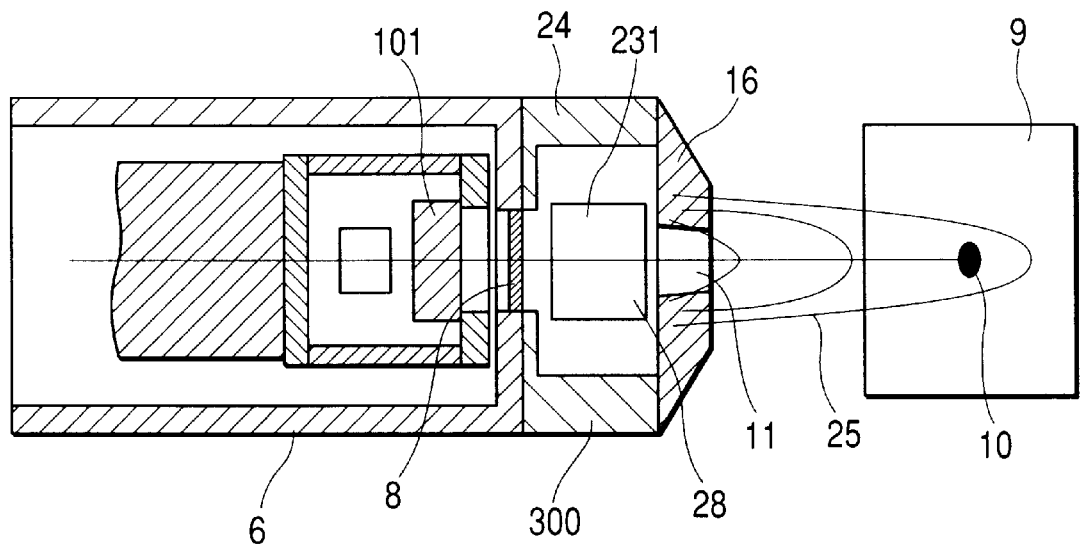
FIG. 22 is a sectional view of an X-ray detector equipped with a conventional electron trap for explaining the leakage magnetic field thereof.

Because the electron trap (FIG. 2) according to the present invention can be set up in the same positional relation to the X-ray crystal as for the conventional type of electron trap (FIG. 22), the conventional apparatus can be improved only by replacing its electron trap part.

Figure 25:
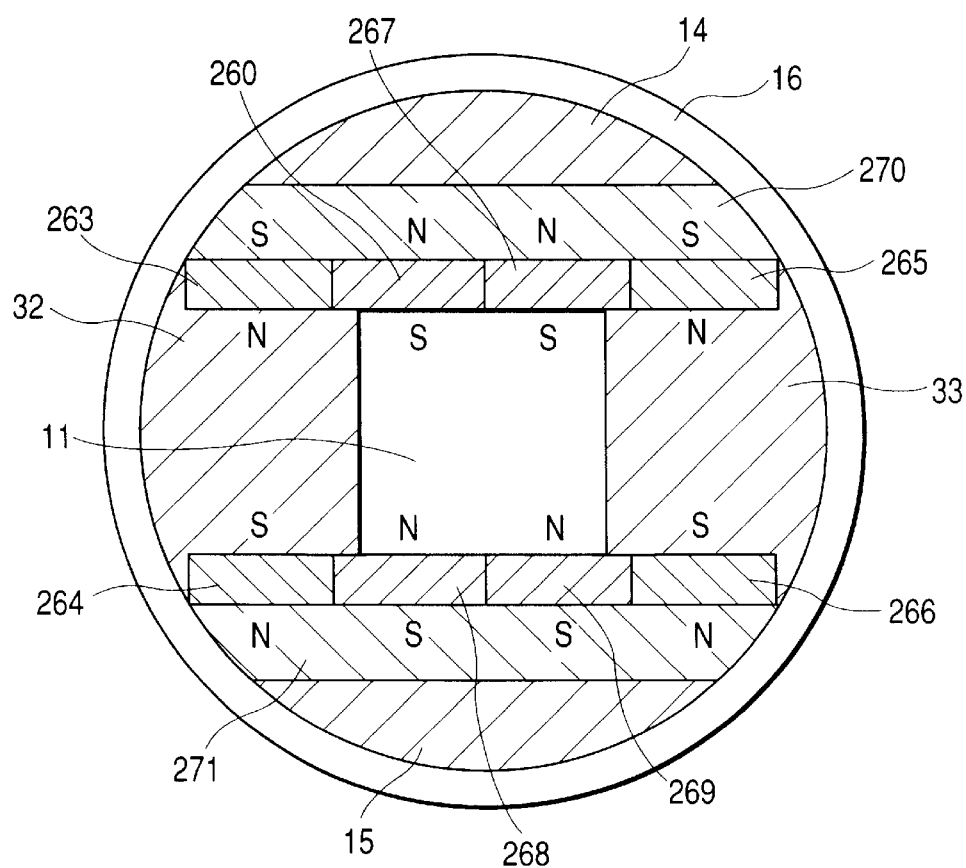
FIG. 25 is a cross sectional view of the electron trap of Embodiment 1 of the present invention.

While, in the foregoing description, the electron trap uses two types of magnets with different dimensions, they can be substituted by magnets of equal dimensions. FIG. 25 shows a vertical sectional view of another electron trap using magnets of equal dimensions. The magnets 260, 267, 268, and 269 have the same polarity as the magnets 261 and 262 shown in FIG. 3, and the magnets used in the electron trap in the foregoing description, but their longitudinal length is half that of the magnets 261 and 262. Specifically, the magnets 260 and 267 replace the magnet 261 shown in FIG. 3, and the magnets 268 and 269 replace the magnet 262. The electron trap with such magnets produces the same effect as previously discussed embodiment.

(Embodiment 2)

Figure 6:
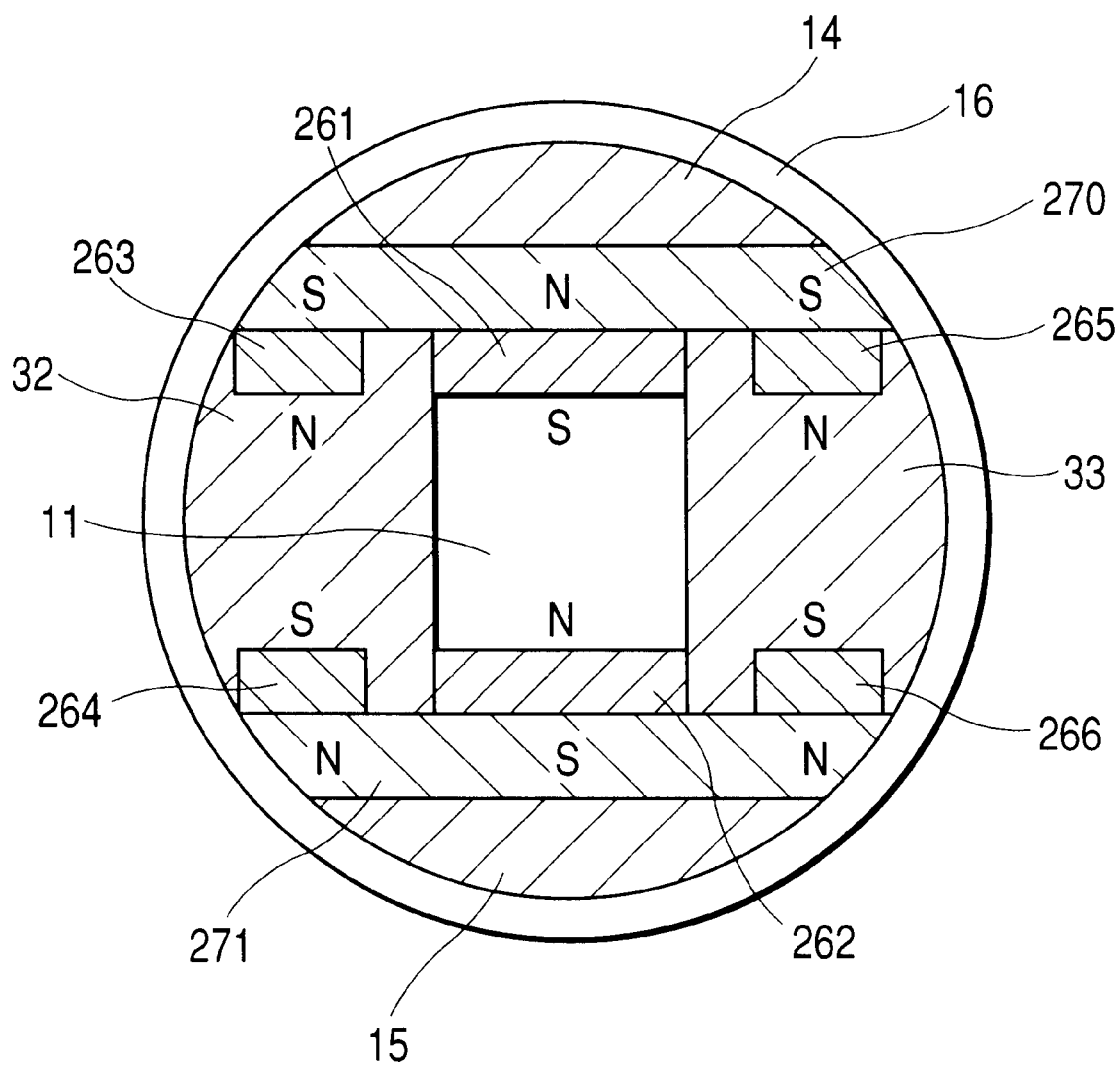
FIG. 6 is a cross sectional view of an electron trap embodied in accordance with a preferred Embodiment 2 of the present invention.

With reference to FIG. 6, the preferred Embodiment 2 of the present invention is described below.

FIG. 6 is a cross sectional view of an electron trap embodied in accordance with Embodiment 2 of the present invention, which shows the trap structure. Using an X-ray crystal with an area larger than that of Embodiment 1 thereby giving a greater solid angle. Embodiment 2 provides an electron trap that is more suitable for detecting X-rays with a greater solid angle.

In Embodiment 2, similarly, the magnetic field to eliminate backscattered electrons is generated by two magnets 261 and 262. To make the electron trap adaptive to the greater solid angle, it is necessary to widen the cross section of the X-ray path hole 11, i.e., to provide more spacing between the magnets 261 and 262. If more spacing is provided between these opposite magnets with the remaining magnets being arranged as described in Embodiment 1, the magnetic field between the adjacent magnets becomes stronger and the field magnetic intensity for eliminating backscattered electrons becomes weaker, and its effective area becomes narrower. In Embodiment 2, thus, spacers 32 and 33 are installed with a given shape, part of which is inserted between the adjacent permanent magnets to separate these magnets.

Permanent magnets 261–266 of the same dimensions as described in Embodiment 1 are employed, and the spacers are installed to separate the adjacent permanent magnets by a 1-mm gap therebetween. The opposite permanent magnets are positioned with a distance of 5.5 mm therebetween. A magnetic flux density of about 0.2 tesla is measured in the center of the X-ray path hole 11. When the X-ray detector with such an electron trap is applied to an electron microscope with the capability of an acceleration voltage of 25 kilovolts, and measurement is made with the X-ray crystal with an effective area of 30 mm square, the influence of backscattered electrons is less than the minimum scale of measurement.

In Embodiment 2, similarly, when viewed from the position of the electron irradiation, four magnets 263–266 are arranged to cancel the magnetic field generated by the permanent magnets 261 and 262 leaked from the X-ray path hole. Thus, at or near the point of electron irradiation, the leakage magnetic field generated by the permanent magnets is substantially zero. Moreover, the magnetic path diameter can be decreased. This effect significantly reduces the disadvantage that an image of the secondary electrons is shifted, deformed, or out of focus by astigmatism when the X-ray detector approaches the specimen.

The values and the outside shape of the electron trap described in Embodiments 1 and 2 of the present invention are not restrictive, and it is self-evident that the present invention still applies if the magnets to cancel the leakage magnetic field from the magnets 261 and 262 are arranged symmetrically with respect to the center axis.

The magnets 261 and 262 are positioned across the X-ray path. In Embodiments 1 and 2 of the present invention, the direction in which an image of the secondary electrons shifts, and the distance of the shift is unchanged even if these magnets are rotated 90 degrees, 180 degrees, or 270 degrees around X-rays path. It is believed that this is because the leakage magnetic field from the electron trap is substantially zero and its interaction with the electron beam almost does not occur. Thus, no matter what orientation around the X-rays path axis the magnets are placed, the present invention is applicable.

(Embodiment 3)

Figure 8:
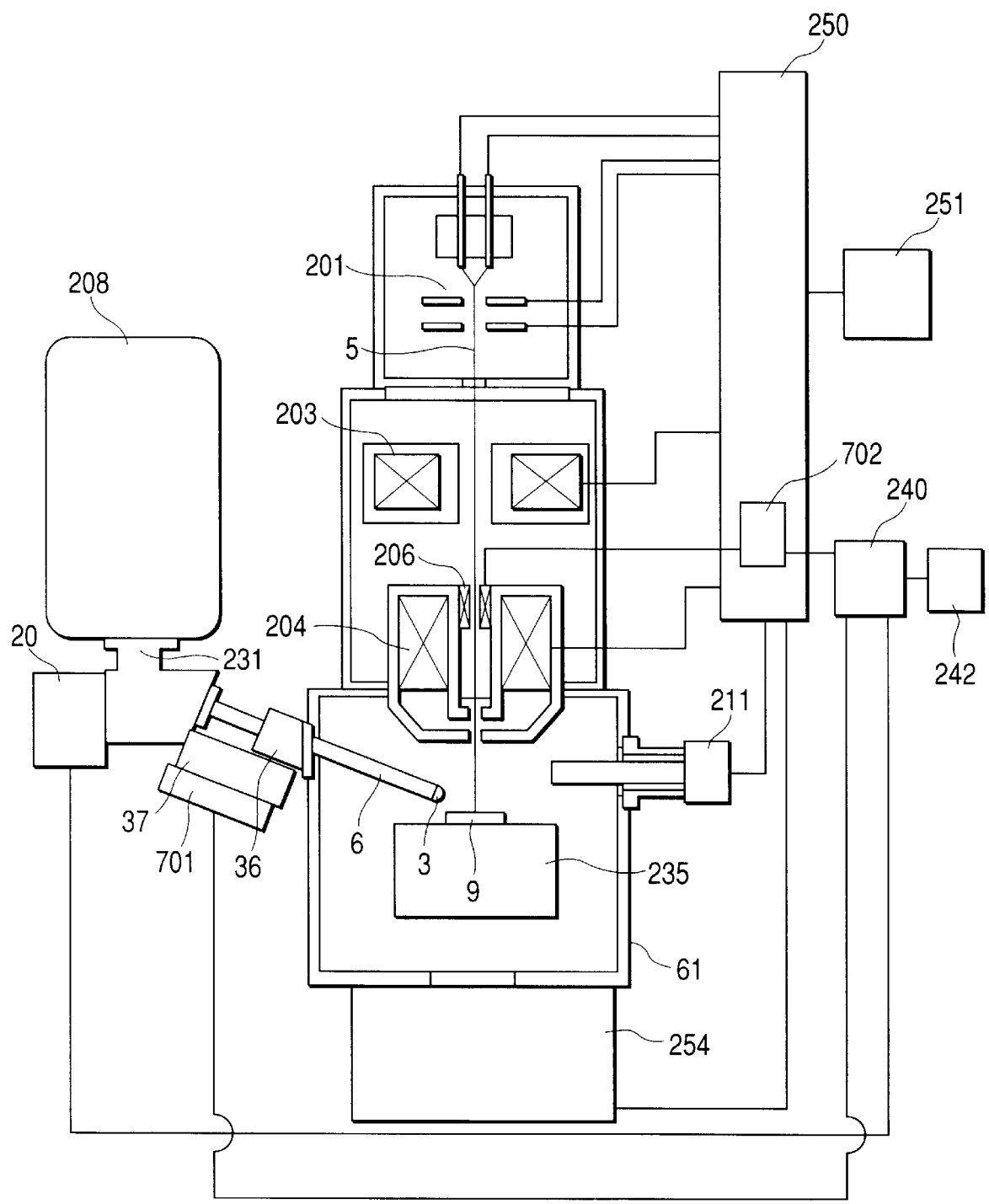
FIG. 8 is a schematic drawing showing an electron microscope on which an X-ray detector with a position sensor embodied in accordance with a preferred Embodiment 3 of the present invention is mounted.

With reference to FIG. 8, the preferred Embodiment 3 of the present invention is described below.

FIG. 8 is a schematic diagram showing an electron microscope on which an X-ray detector mounted with an electron trap, which is a preferred Embodiment 3 of the present invention. The X-ray detector comprises the electron trap 3, a cylindrical chamber 6 in which an X-ray crystal is housed, a chamber 231, flanges 36, a moving mechanism 37, a liquid nitrogen reservoir 208, a circuit block of pre-amplifier 20, an X-ray pulse processor 240, and an I/O unit 242. The chamber 6 and chamber 231 are evacuated and sealed. The same electron trap 3 described in the section of Embodiment 1 is used. The moving mechanism 37 is worked to prolong or retract the tip of the X-ray detector 5 from the specimen stage. Using this mechanism, the operator makes the tip approach a specimen 9 when measurement is made and keep the tip away from the specimen when measurement is not performed. In Embodiment 3, a position sensor 701 is mounted to the moving mechanism 37 so that the position of the tip of the X-ray detector (as the tip is protruded) can be sensed. The information of the position of the tip being protruded is processed by the X-ray pulse processor 240 and converted into control signals that are transferred to the scanning coil control circuit 702 of the electron microscope.

When the tip of the X-detector is protruded, an image of the secondary electrons shifts and the shift distance increases as the tip is approaching the specimen. In Embodiment 3, the shift distance of the image of the secondary electrons, relative to the position of the tip being protruded, is measured beforehand. The relationship between the shift distance and the tip position are recorded into the X-ray pulse processor 240. Based on the data, the tip position information sensed by the position sensor 701 is converted into signals that are transferred to the scanning coil control circuit. According to these signals, the scanning position is changed and the shift of the image of the secondary electrons due to the protrusion of the tip of the X-ray detector is corrected. Adjustment can thus be made so that the image apparently does not shift. Consequently, convenience of use is enhanced.

By using the electron trap described in Embodiments 1 and 2, the disadvantage that an image of the secondary electrons is shifted, deformed, or out of focus by astigmatism when the X-ray detector approaches the specimen is significantly reduced, and correction of the shift distance according to Embodiment 3 can be realized. For conventional X-ray detectors, such correction is difficult due to a large shift.

While, in the foregoing description of Embodiment 3 of the present invention, correction is made, based on the relationship between the tip position of the X-ray detector and the shift distance of the image of the secondary electrons, correction also can be made by taking real-time measurements of the shift distance of the image of the secondary electrons and analyzing the image each time the tip of X-ray detector is protruded.

(Embodiment 4)

Figure 9:
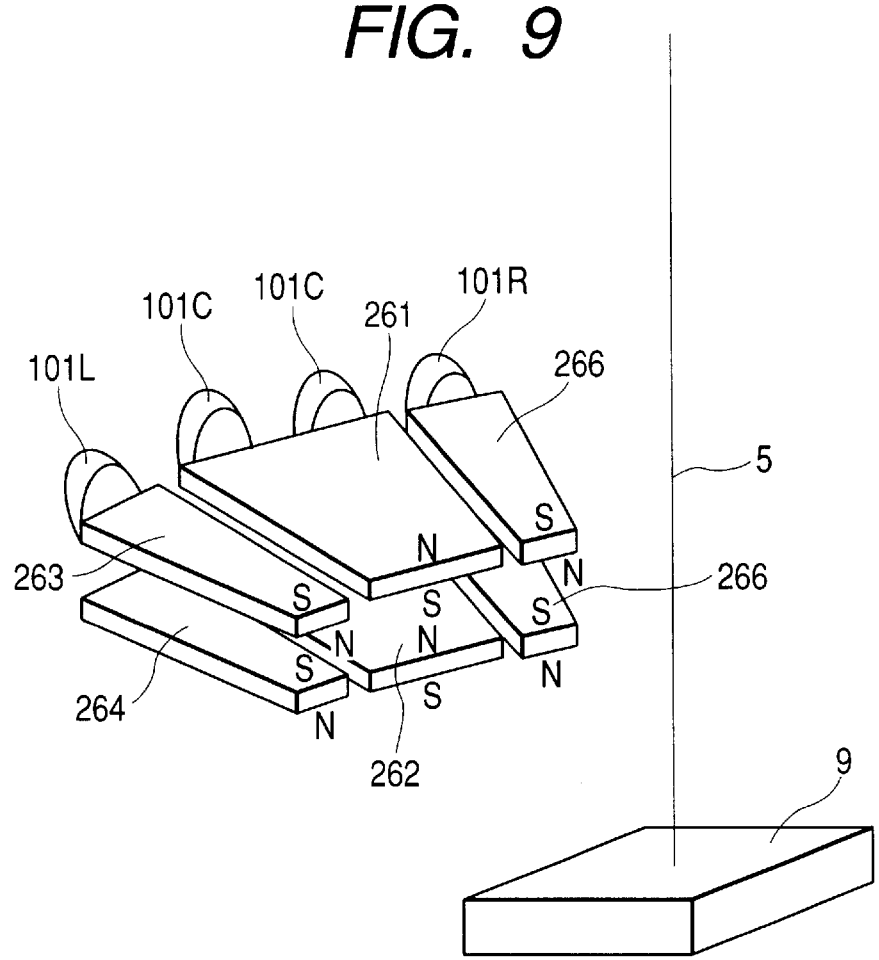
FIG. 9 is a schematic perspective view of an electron trap embodied in accordance with a preferred Embodiment 4 of the present invention.
Figure 10:
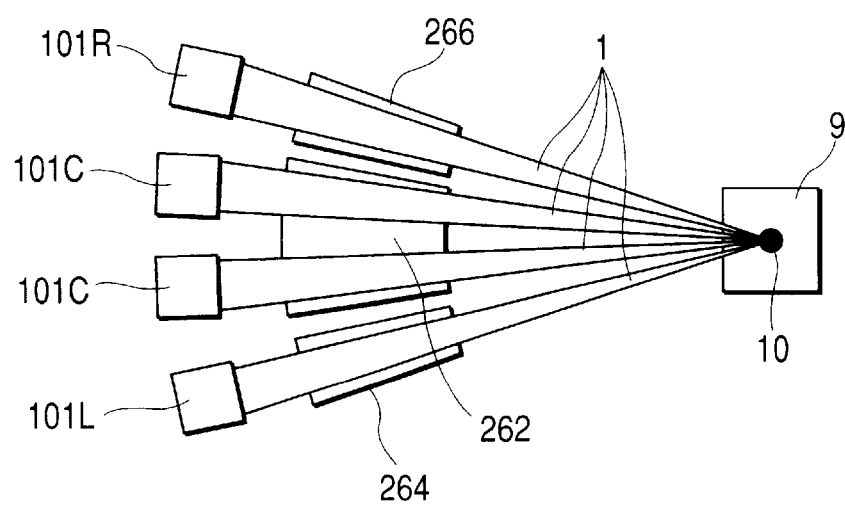
FIG. 10 is a sectional view of the electron trap of Embodiment 4 of the present invention.

With reference to FIGS. 9 and 10, the preferred Embodiment 4 of the present invention is described below.

FIG. 9 is a perspective view of an electron trap embodied according to a preferred Embodiment 4 of the invention, which shows the trap structure. FIG. 10 is a sectional view of the electron trap taken at the plane including the point of electron irradiation and the centerlines of X-ray crystals.

The present invention in Embodiment 4 applies four X-ray crystals. The electron trap of the X-ray detector of Embodiment 4 uses magnetic fields generated by a pair of sectorial permanent magnets 261 and 262, a pair of magnets 263 and 264, and a pair of magnets 265 and 266, each of the last two pairs is placed on one end of the magnet pair 261 and 262 as shown in FIG. 10.

The magnets are positioned such that the orientations of their magnetic poles are as follows: the S pole surface of the magnet 261 and the N pole surface of the magnet 262 face toward each other, the N pole surface of the magnet 263 and the S pole surface of the magnet 264 face toward each other, and the N pole surface of the magnet 265 and the S pole surface of the magnet 266 face toward each other. The area of the magnets 263–266 is half the dimensions of the magnets 261 and 262. The magnets 261, 263, and 265 are bonded to one magnetic path (not shown) and the magnets 262, 264, and 266 are bounded to another magnetic path (not shown).

On the sides of the space between the magnet 261 and the magnet 262 (where no magnets exist), two aluminum spacers (not shown) are installed to enclose the space, as described in Embodiment 1. In Embodiment 4, one of the spacers has a hole in the center of the space between the magnet 263 and the magnet 264, and the other spacer has a hole in the center of the space between the magnet 265 and the magnet 266, so that X-rays 1 shown in FIG. 10 are allowed to pass though the thus formed paths.

X-rays 1 passing through the space between the magnet 261 and the magnet 262 arrive at two X-ray crystals 101C as incident rays. X-rays 1 passing through the space between the magnet 263 and the magnet 264 arrive at an X-ray crystal 101L, and X-rays 1 passing through the space between the magnet 265 and the magnet 266 arrive at an X-ray crystal 101R.

In Embodiment 4, similarly, when viewed from the electron beam, four magnets 263–266 are arranged to cancel the magnetic field generated by the permanent magnets 261 and 262 leaking from the X-ray path holes (not shown). Thus, at or near the point of electron irradiation, the leakage magnetic field generated by the permanent magnets is substantially zero. Moreover, the magnetic path diameter can be decreased. This effect significantly reduces the disadvantage that an image of the secondary electrons is shifted, deformed, or out of focus by astigmatism, which takes place when the X-ray detector approaches the specimen. Furthermore, the use of four X-ray crystals multiplies the efficiency as if detecting four times.

(Embodiment 5)

Figure 11:
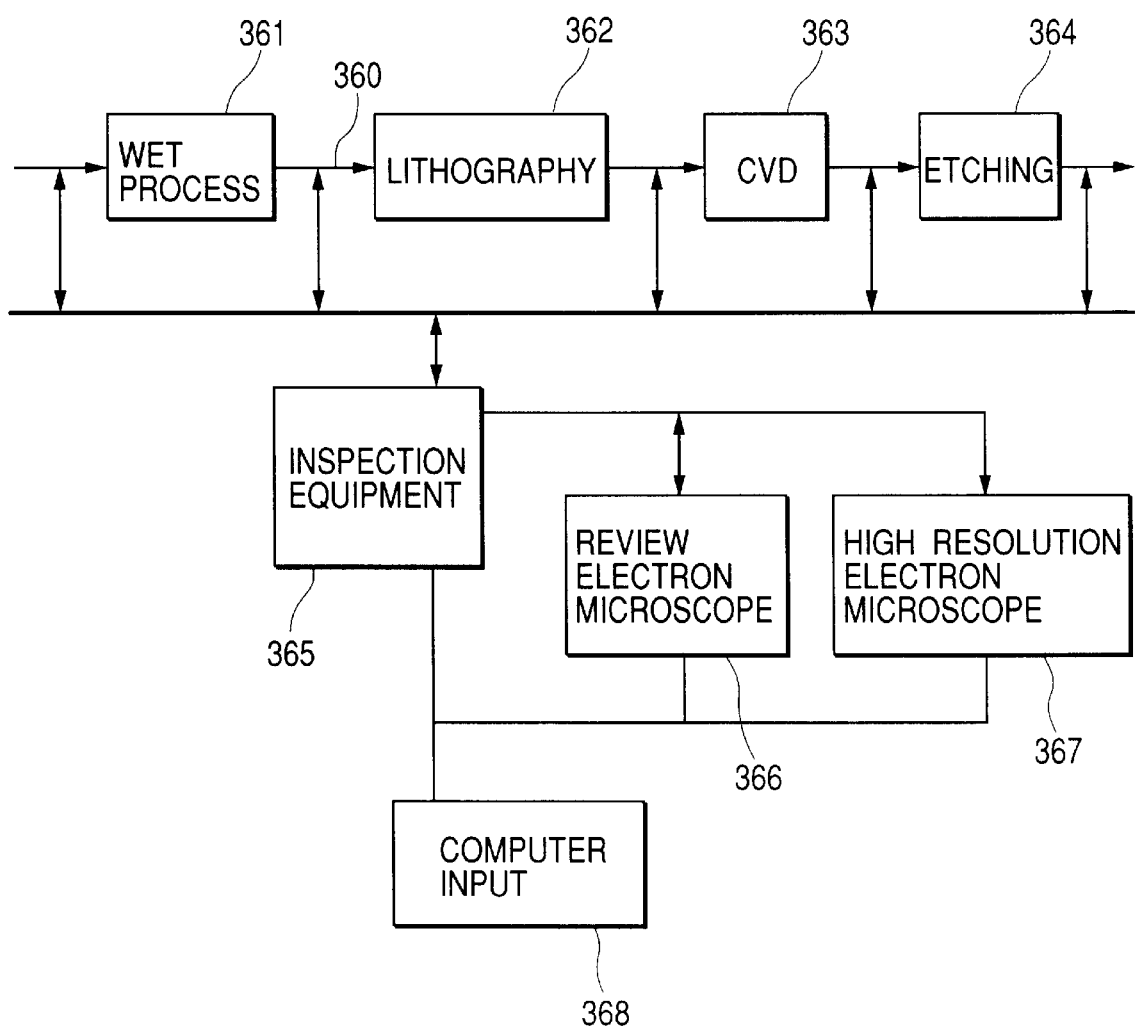
FIG. 11 is a flow chart for explaining a preferred Embodiment 5 of the present invention.

With reference to FIG. 11, the preferred Embodiment 5 of the present invention is described below. FIG. 11 is a diagram showing part of a semiconductor inspection system and the semiconductor manufacturing equipment including an electron microscope equipped with an X-ray detector with an electron trap of the present invention.

In production of large scale integrated (LSI) circuits, such as dynamic random access memory units, the ratio of the number of non-defective units to the number of units to be produced is called a yield. Defects from foreign matter deposited to circuit elements are regarded as a factor decreasing the yield. The foreign matter may be (1) substances deposited to the inner walls of semiconductor manufacturing equipment 361–364 during processing required to form circuits, such as etching, ion implantation, and depositing a film or layer, (2) substances deposited during the carriage of semiconductor wafers on which circuits are formed through wafer transport routes 360, or (3) peel-off materials of patterns formed on the semiconductor wafers during the manufacturing process. It is important to identify the sources of foreign matter so as to control the sources to enhance the yield in a short period.

In Embodiment 5 of the present invention, a semiconductor wafer is extracted at the end of each manufacturing process of the semiconductor manufacturing equipment 361–364 as shown in FIG. 11, which can be substituted by any semiconductor manufacture procedures. First, the wafer is checked for any deposited foreign matter regarding its type and shape, and its coordinates are identified by a particle/pattern inspection equipment 365 with an optical microscope and a scanning electron microscope (observation without contacting the wafer). The main role of this inspection equipment 365 is quickly inspect wafers so as to detect any foreign matter deposit and obtain data of its outline shape and position.

In the next step, a review electron microscope 366 is used to obtain detailed information, such as three-dimensional shapes, and compositions of foreign matter deposits. Furthermore, a high-resolution electron microscope 367 equipped with a specimen-making apparatus that cuts a part of a foreign matter deposit from a wafer to make a specimen for detailed inspection of a cross-section of the foreign matter deposit.

The information on foreign matter deposit shapes and coordinates is put under centralized management by a computer 368. When a foreign matter deposit is specified by the review electron microscope 366, it is observed promptly by referring to its the coordinates obtained by the particle/pattern inspection equipment 365. It is important to identify foreign matters on semiconductor wafers thereby improving the yield of LSI semiconductor products as described above. During work routine, it is often to encounter several hundreds to several thousands of foreign matters depositing on a wafer. The composition of the foreign matters is analyzed by the X-ray detector mounted on the electron microscopes. On the review electron microscope 366 and the high-resolution electron microscope 367 in Embodiment 5, the X-ray detector with the electron trap, a special feature of the present invention, is mounted. By using this X-ray detector, the microscopes can approach a specimen sufficiently close. Because the solid angle of the detector within sight of the specimen is set larger, detection of characteristic X-rays from the specimen is performed at a higher rate, and the time required for X-ray analysis is much shortened.

Heretofore, it took several hours to complete X-ray analysis for such several hundreds to thousands of foreign matter deposits and a limit is set to the number of wafers that can be put to the measurement process. By using the X-ray detector of the present invention, the approach distance from the specimen to the detector can be enhanced from 40 mm to 16 mm. In other words, the solid angle of the detector within sight of the specimen is multiplied six times that for conventional X-ray detectors. As a consequence, the analysis can be completed in several tens of minutes; i.e., the time required is cut to one sixth of the time required for conventional X-ray detectors. The throughput of the analysis is enhanced, which leads to rapid and drastic yield improvement for producing semiconductor circuit packages. Moreover, as the dimensions of the semiconductor circuits become smaller, the dimensions of foreign matter deposits to be detected also become smaller. By applying the present invention, the detection sensitivity becomes several times higher than that of conventional X-ray detectors. Even foreign matter deposits of very small dimensions are detected.

(Embodiment 6)

Figure 12:
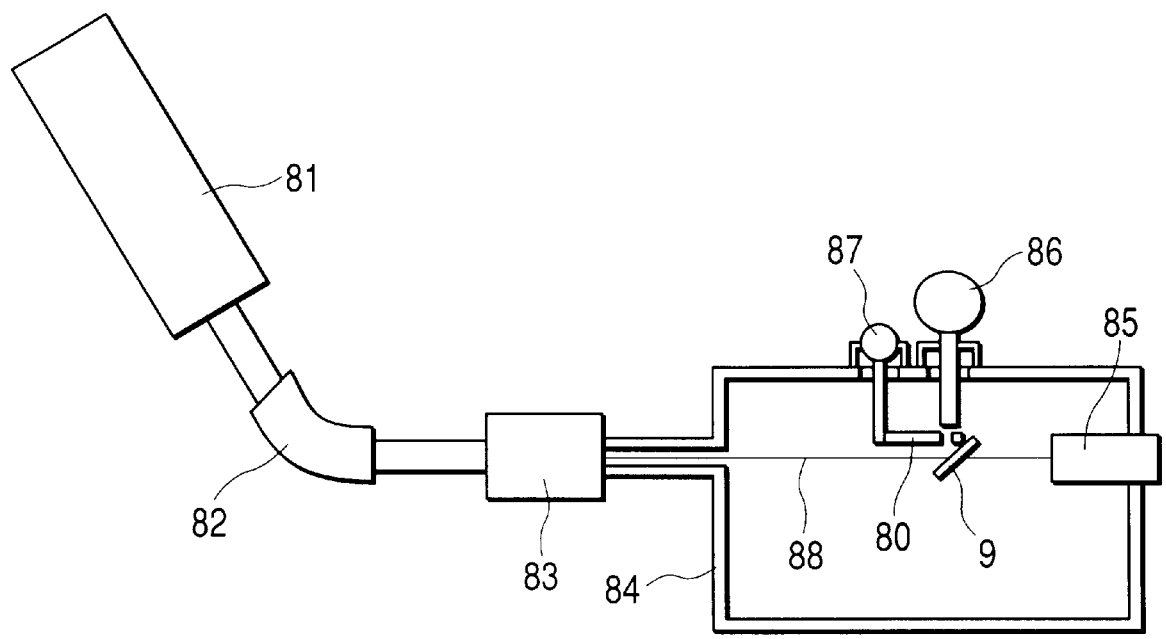
FIG. 12 is an overall structural drawing of the apparatus embodied in accordance with a preferred Embodiment 6 of the present invention.
Figure 13:
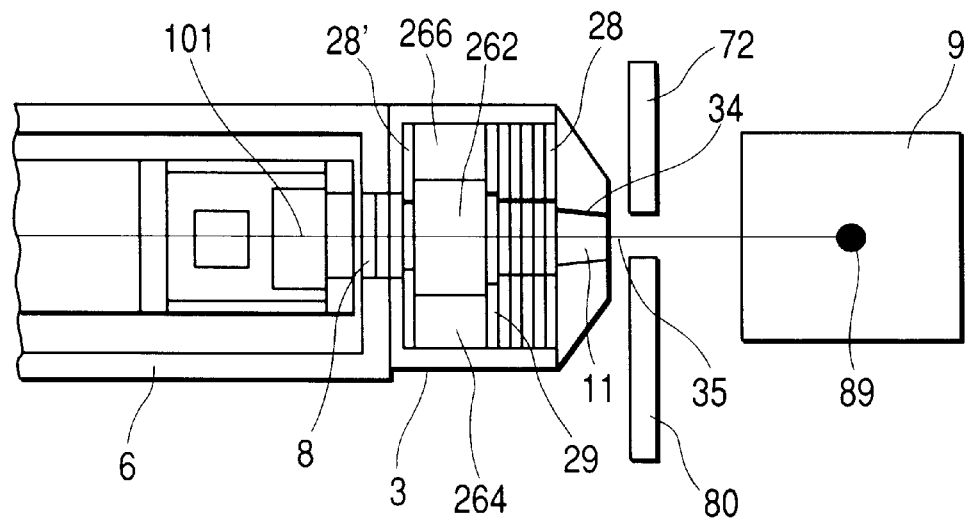
FIG. 13 is a vertical sectional view of the X-ray detector in Embodiment 6 of the present invention including an X-ray detecting element and a specimen.

With reference to FIGS. 12 and 13, the preferred Embodiment 6 of the present invention is described below. FIG. 12 is a structural drawing of a particle-induced X-ray emission/spectroscopy apparatus into which the X-ray detector of the present invention is integrated. FIG. 13 is a sectional view of the X-ray detector, showing the positional relation between its tip and a specimen.

The particle-induced X-ray emission/spectroscopy provides a beam of ions 88 to strike on a specimen 9, measures X-rays emitted from the specimen 9, and analyze the specimen and its elements. The beam of ions is generated as follows. An ion accelerator 81 generates accelerated ions from which a discriminator 82 extracts ions having a specific energy quantity, and a convergence lens 83 converges the ions into a beam.

As for ion energy and ion types, protons and alpha particles of 1–3 MeV are used. Ion beam current is measured by a Faraday cup 85 and used as calibration data. The X-rays emitted from the specimen are measured by a semiconductor detector 86 which is cooled by liquid nitrogen. Referring to FIG. 13, a metal plate 72 cooled by liquid nitrogen is installed between the specimen and the X-ray detector. The metal plate adsorbs neutral particles emitted from the specimen to reduce the contamination of the tip and X-ray window 8 of the X-ray detector. On the tip of the X-ray detector, an electron trap comprising permanent magnets 262, 264, and 266 (the trap having a total of six magnets, but the remaining three magnets at the rear are not shown) is installed as is the case in Embodiment 1. Secondary electrons and ions from the specimen are eliminated by the electron trap.

In Embodiment 6, similarly, when viewed from the ion beam source, four magnets 263–266 are arranged to cancel the magnetic field generated by the permanent magnets 261 and 262 leaked from the X-ray path hole 11. Thus, at or near the point of electron irradiation, the leakage magnetic field generated by the permanent magnets is substantially zero. Moreover, the magnetic path diameter is decreased. This effect makes reduces an adverse effect on the ion beam, which takes place when the X-ray detector approaches the specimen.

Consequently, the operator can adjust the X-ray detector to approach the specimen much closer than the conventional X-ray detectors, which multiplies the detection sensitivity thereby reducing the required ion beam current and making the apparatus smaller.

(Embodiment 7)

Figure 14:
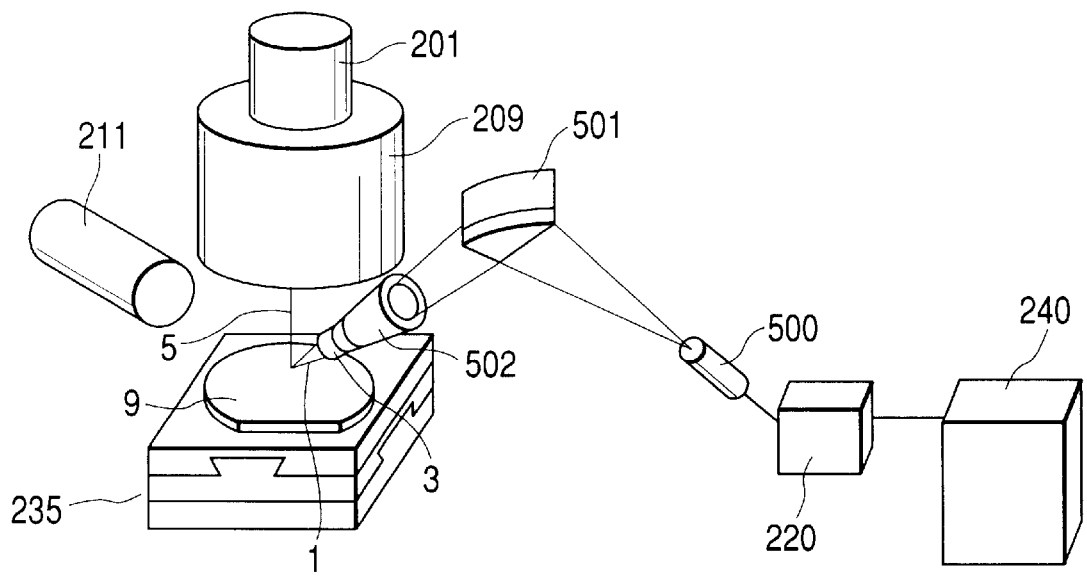
FIG. 14 is a perspective view of an inspection equipment embodied in accordance with a preferred Embodiment 7 of the present invention.

With reference to FIG. 14, the preferred Embodiment 7 of the present invention is described below. FIG. 14 depicts an inspection equipment including an electron microscope equipped with an X-ray detector with an electron trap of the present invention. In Embodiment 7, the present invention is applied to an X-ray spectrometry of a wavelength dispersive type.

By sending a beam of primary electrons 5 to strike a specimen 9, X-rays from the specimen 9 are dispersed in a spectrum by a grating 501. A proportional counter 500 detects the spectrum of X-rays.

A single curved crystal or an artificial laminate is used as the grating 501. The grating 501 and the proportional counter 500 move together to perform wavelength scanning. Between the grating 501 and the specimen 9, the electron trap 3 and a collimator 502 the present invention are positioned. The internal structure of the electron trap 3 is the same as that described in Embodiment 1.

The collimator 502 collects X-rays from the specimen and leads the X-rays to the grating 501. The collimator is a glass cylinder with a parabolic inside surface on which a metallic mirror is formed by vacuum evaporation of metal. This structure efficiently collects X-rays from the specimen. A charged particle eliminator is provided to prevent backscattered electrons by the specimen from entering the collimator 502 and the grating 501. Consequently, the electrons will not strike against the collimator 502 and the grating 501 to turn into undesired X-rays. Thus, X-rays are detected with little noise. Due to the use of the charged particle eliminator with a little leakage magnetic field of the invention, influence on the beam of electrons 5 is small. This is particularly effective even if the acceleration voltage of the primary electron beam is set as low as several kilovolts or lower to reduce damage to the specimen, and X-ray detection can be performed while the image resolution of the secondary electrons is high.

By using this X-ray detector, the operator can adjust its tip to approach the specimen sufficiently close without any concern of an adverse effect on the primary electron beam. Because the solid angle of the detector within sight of the specimen is set larger, detection of characteristic X-rays from the specimen is performed at a higher rate and the time required for X-ray analysis is much shortened.

(Embodiment 8)

Figure 15:
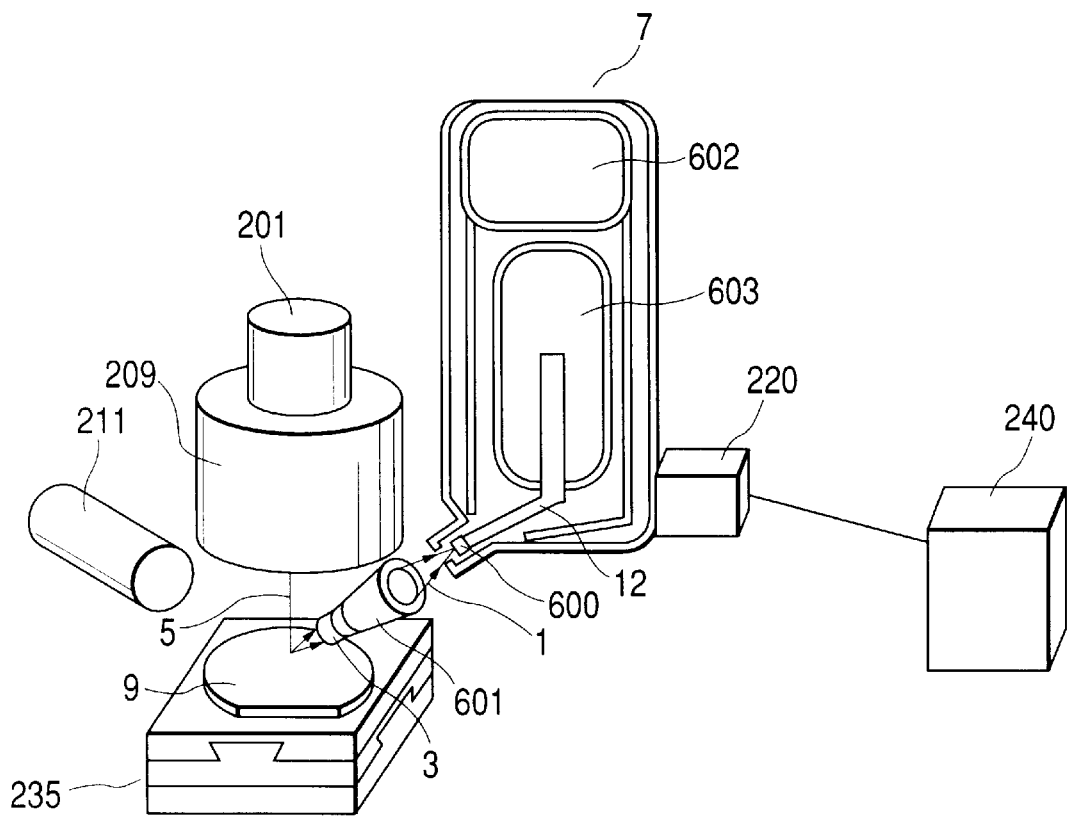
FIG. 15 is a perspective view of another inspection equipment embodied in accordance with a preferred Embodiment 8 of the present invention.
Figure 16:
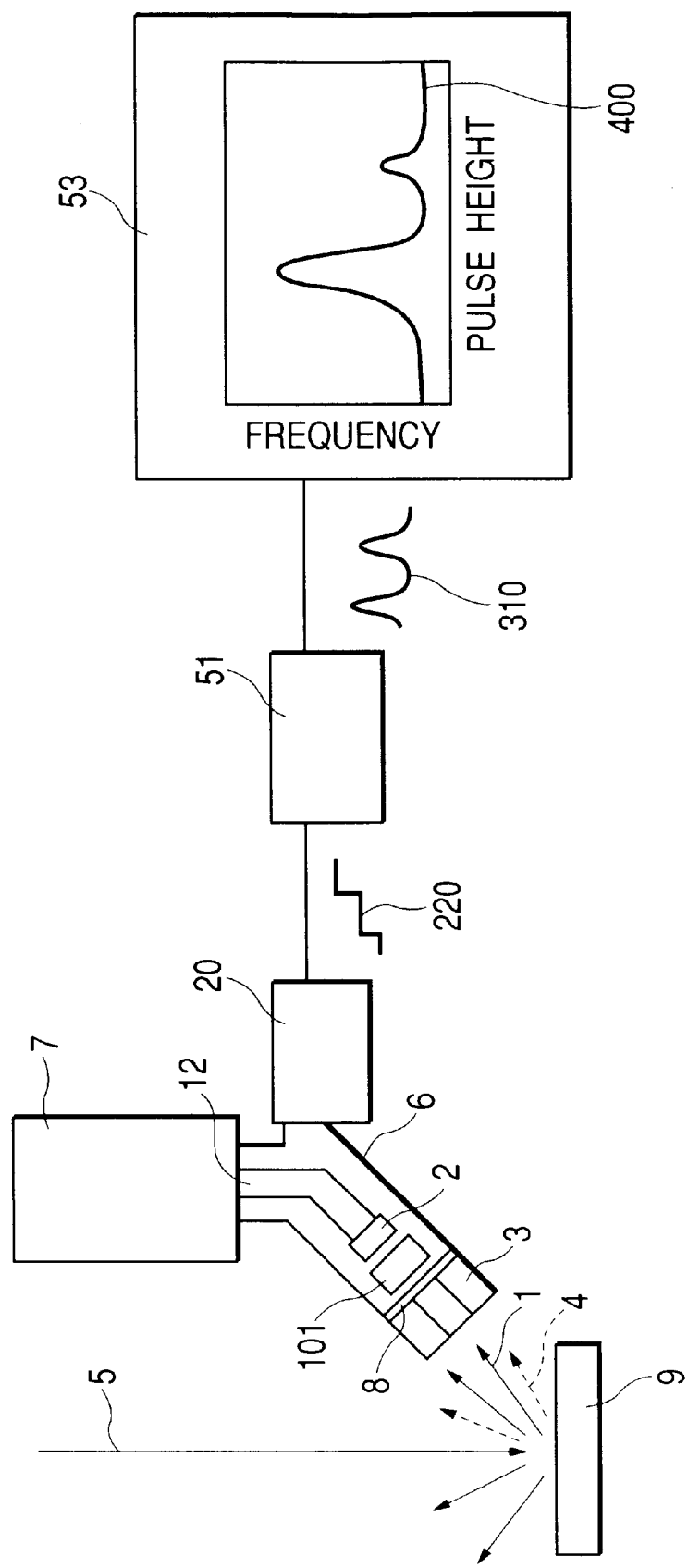
FIG. 16 is a structural drawing representing the principles and structure of a conventional type of X-ray detector.

With reference to FIG. 15, the preferred Embodiment 8 is described below. FIG. 15 depicts an electron microscope on which a cryogenic X-ray detector with an electron trap of the present invention is mounted. The cryogenic X-ray detector uses a detector 600 (called a bolometer) cooled to ultra-low temperature below 100 milli-Kelvin by liquid nitrogen 602 and liquid helium 603. Taking advantage of that the temperature of the detector 600 changes when X-rays 1 arrive at this detector 600, the energy of the incident X-rays is measured with regard to the degrees of temperature change. In this way, the cryogenic X-ray detector detects X-rays with energy resolution that is one fiftieth or below of that of the semiconductor detector. Usually, the X-ray sensitive area of the cryogenic X-ray detector is smaller than that of the semiconductor detector. Thus, a focusing lens 601 inserted between the detector 600 and the specimen 9 converges the X-rays emitted from the specimen 9 to the detector 600 such that the solid angle of detection is improved.

Furthermore, the electron trap 3 of the present invention is installed to prevent backscattered electrons by the specimen from entering the detector 600 and focusing lens 601 thereby reducing noise. The structure of the electron trap 3 is the same as that of the electron trap in Embodiment 1. By using this X-ray detector, the operator can adjust its tip to approach the specimen sufficiently close. Because the solid angle of the detector within sight of the specimen is set larger, the detection of characteristic X-rays from the specimen is performed at a higher rate, and the time required for X-ray analysis is much shortened.

If the acceleration voltage of the primary electron beam is set as low as several kilovolts or lower to reduce damage to the specimen, the energy of emitted X-rays is also restricted. For an element that does not emit X-rays called K-lines, which are normally used for X-ray analysis, low-energy X-rays such as L-lines and M-lines are used for analysis.

The X-ray detector used in Embodiments 5 and 6 enables X-ray detection with very high-energy resolution, even if a semiconductor detector is used such that X-ray peaks overlap to make analysis difficult. Even if a beam of primary electrons with low acceleration voltage is used, the shape and orbit of the primary electron beam remains unchanged, according to the present invention, and thus satisfactory specimen observation can still be performed.

According to the present invention, satisfactory images of the secondary electrons can be obtained due to the following advantages. Even when the X-ray detector approaches closely to a specimen, the leakage magnetic field from the electron trap on its tip is suppressed down to a negligible level at or near the point of electron irradiation. The mag- netic path diameter thus can be decreased. Consequently, an image of the secondary electrons is not affected by its significant shift, deformation, and out-of-focus due to the astigmatism. Furthermore, the shift of the image of the secondary electrons can easily be corrected. Because the X-ray detecting element can be moved to approach the specimen closely, the detection sensitivity can be multiplied. Moreover, improvement to a conventional X-ray detector can be made by only replacing its electron trap part.

The foregoing invention has been described in terms of preferred embodiments. However, those skilled in the art will recognize that many variations of such embodiments exist. Such variations are intended to be within the scope of the present invention and the appended claims.

What is claimed is:

1. A charged particle trap for trapping any undesired charged particles in detecting X-rays from a specimen, comprising:

a first pair of permanent magnets placed above and below a X-ray path hole such that inner surfaces of opposite polarities of the first pair of permanent magnets facing toward each other across the X-ray path hole;

a second pair of permanent magnets each of which is placed on one end of one of said first pair of permanent magnets along a direction parallel with the X-ray path; and a third pair of permanent magnets each of which is placed on one end of the other of said first pair of permanent magnets along a direction parallel with the X-ray path, wherein the X-ray path hole is placed in front of a X-ray crystal for receiving and transforming X-rays into electronic signals.

2. The charged particle trap according to claim 1, wherein the undesired charged particles include back-scattered charged particles which are back-scattered by the specimen after the specimen is struck by a beam of charged particles.

3. The charged particle trap according to claim 1, wherein inner surfaces of said second pair permanent magnets facing toward inner surfaces of said third pair of permanent magnets being of opposite polarities, and polarities of the inner surfaces of said second and third pairs permanent magnets alternate with the adjacent one of the first pair of permanent magnets.

4. The charged particle trap according to claim 1, wherein the magnetic force of the magnetic poles of said first pair of permanent magnets is substantially equal to the sum of the magnetic forces of the magnetic poles of said second and third permanent magnets.

5. The charged particle trap according to claim 1, wherein the opposite surfaces of said second and third permanent magnets have substantially equal areas and the area of the opposite surfaces of said first pair of permanent magnets is approximately double the areas of the opposite surfaces of said second and third permanent magnets.

6. The charged particle trap according to claim 1, wherein said second and third permanent magnets of opposite polarities are separated by spacers made of a non-magnetic material.

7. An X-ray detector, comprising:

an X-ray crystal for receiving and transforming X-rays from a specimen into electronic signals;

an X-ray path hole placed in front of the X-ray crystal for guiding the X-rays to the X-ray crystal; and a charged particle trap for trapping any undesired charged particles, which includes:

a first pair of permanent magnets placed above and below the X-ray path hole such that inner surfaces of opposite polarities of the first pair of permanent magnets facing toward each other across the X-ray path hole;

a second pair of permanent magnets each of which is placed on one end of one of said first pair of permanent magnets along a direction parallel with the X-ray path; and a third pair of permanent magnets each of which is placed on one end of the other of said first pair of permanent magnets along a direction parallel with the X-ray path.

8. The X-ray detector according to claim 7, wherein the undesired charged particles include back-scattered charged particles which are back-scattered by the specimen after the specimen is struck by a beam of charged particles.

9. The X-ray detector according to claim 7, wherein inner surfaces of said second pair permanent magnets facing toward inner surfaces of said third pair of permanent magnets being of opposite polarities, and polarities of the inner surfaces of said second and third pairs permanent magnets alternate with the adjacent one of the first pair of permanent magnets.

10. The X-ray detector according to claim 7, wherein the magnetic force of the magnetic poles of said first pair of permanent magnets is substantially equal to the sum of the magnetic forces of the magnetic poles of said second and third permanent magnets.

11. The X-ray detector according to claim 7, wherein the opposite surfaces of said second and third permanent magnets have substantially equal areas and the area of the opposite surfaces of said first pair of permanent magnets is approximately double the areas of the opposite surfaces of said second and third permanent magnets.

12. The X-ray detector according to claim 7, wherein said second and third permanent magnets of opposite polarities are separated by spacers made of a non-magnetic material.

13. An apparatus for detecting X-rays with charged particles, comprising:

a specimen stage on which a specimen is rested;

a charged particle beam irradiation unit for generating a beam of charged particles to strike on the specimen;

an X-ray crystal for receiving and transforming X-rays from the specimen into electronic signals; and an charged particle trap for trapping undesired charged particles which includes:
  a first pair of permanent magnets located across the X-ray path hole;
  a second pair of permanent magnets each of which is placed on one end of one of said first pair of permanent magnets along a direction parallel with the X-ray path; and
  a third pair of permanent magnets each of which is placed on one end of the other of said first pair of permanent magnet along a direction parallel with the X-ray path, wherein said second and third pairs of permanent magnets generate a magnetic field that cancels a leakage magnetic field generated by said first pair of permanent magnets.

14. The apparatus for detecting X-rays with charged particles according to claim 13, wherein the undesired charged particles include back-scattered charged particles which are back-scattered by the specimen after the specimen is struck by the beam of charged particles.

15. The apparatus for detecting X-rays with charged particles according to claim 13, wherein said first pair of permanent magnets are located such that inner surfaces of opposite polarities of the first pair of permanent magnets facing toward each other, and said second and third permanent magnets are located such that their inner surfaces facing toward each other having opposite polarities and alternate with the adjacent one of the first pair of permanent magnets.

16. The apparatus for detecting X-rays with charged particles according to claim 13, wherein the magnetic force of the magnetic poles of said first pair of permanent magnets is substantially equal to the sum of the magnetic forces of the magnetic poles of said second and third permanent magnets.

17. The apparatus for detecting X-rays with charged particles according to claim 13, wherein inner surfaces of said second pair permanent magnets facing toward inner surfaces of said third pair of permanent magnets being of opposite polarities, and polarities of the inner surfaces of said second and third pairs permanent magnets alternate with the adjacent one of the first pair of permanent magnets.

18. The apparatus for detecting X-rays with charged particles according to claim 13, wherein said second and third permanent magnets of opposite polarities are separated by spacers made of a non-magnetic material.

19. The apparatus for detecting X-rays with charged particles according to claim 13, further comprising:

an electronic signal counter for counting the electronic signals outputted from the X-ray crystal; and a display unit for displaying an image of countering results outputted from the electronic signal counter.

20. The apparatus for detecting X-rays with charged particles according to claim 19, further comprising:

a scanning controller for controlling the charged particle beam irradiation unit to focus with a lens and the beam of charged particles to scan the specimen set on said specimen stage;

a synchronizer for synchronizing the display unit and the scanning controller thereby synchronizing the displayed image with the scanned portion of the specimen; and a moving mechanism for moving a charged particle beam irradiation relatively to a position of the charged particle trap.

* * * * *